(12) United States Patent
Ammendola et al.

(10) Patent No.: US 8,653,138 B2
(45) Date of Patent: *Feb. 18, 2014

(54) CALCIUM SALTS OF COMPOUNDS AS ANTI-INFLAMMATORY, IMMUNOMODULATORY AND ANTI-PROLIFERATORY AGENTS

(75) Inventors: Aldo Ammendola, Graefelfing (DE); Julia Diederichs, Munich (DE); Johann Leban, Planegg-Martinsried (DE); Daniel Vitt, Germering (DE)

(73) Assignee: 4SC MG, Planegg-Martinsried (DE)

( * ) Notice: Subject to any disclaimer, the term of this patent is extended or adjusted under 35 U.S.C. 154(b) by 129 days.

This patent is subject to a terminal disclaimer.

(21) Appl. No.: 13/174,899

(22) Filed: Jul. 1, 2011

(65) Prior Publication Data

US 2012/0029034 A1    Feb. 2, 2012

Related U.S. Application Data

(60) Provisional application No. 61/360,670, filed on Jul. 1, 2010.

(51) Int. Cl.
*A61K 31/195* (2006.01)
*A61K 31/19* (2006.01)
*C07C 229/00* (2006.01)

(52) U.S. Cl.
USPC ........... 514/563; 514/568; 514/561; 514/557; 562/498; 562/433; 562/400

(58) Field of Classification Search
None
See application file for complete search history.

(56) References Cited

U.S. PATENT DOCUMENTS

| | | | |
|---|---|---|---|
| 7,176,241 B2 * | 2/2007 | Leban et al. | 514/615 |
| 7,247,736 B2 * | 7/2007 | Leban et al. | 549/71 |
| 8,354,433 B2 * | 1/2013 | Vitt et al. | 514/332 |
| 2003/0203951 A1 * | 10/2003 | Leban et al. | 514/372 |

OTHER PUBLICATIONS

"Salt Selection and Optimisation Procedures for Pharmaceutical New Chemical Entities" by Bastin et al., Org. Proc. Res. Dev. 4, 427-35 (2000).*
"Occurrence of Pharmaceutically Acceptable Anions and Cations in the Cambridge Structural Database" by Haynes et al., J. Pharm. Sci. 94, 2111-20 (2005).*

* cited by examiner

*Primary Examiner* — Brandon Fetterolf
*Assistant Examiner* — Theodore R West
(74) *Attorney, Agent, or Firm* — Millen, White, Zelano & Branigan, P.C.

(57) ABSTRACT

The present invention relates to calcium salts of compounds of the general formula (I)

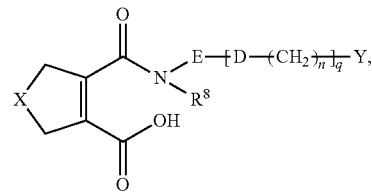

wherein
X is selected from the group consisting of $CH_2$, S, or O;
D is O or S;
$R^8$ is hydrogen or alkyl;
E is an optionally substituted phenylene group;
Y is a monocyclic or bicyclic substituted or unsubstituted 6-9 membered ring system which may contain one or more heteroatoms selected from N or S and which contains at least one aromatic ring;
n is 0 or 1, and
q is 0 or 1;
with the proviso that compounds wherein X=$CH_2$, q=0, Y=unsubstituted phenyl and E=unsubstituted phenylene are excluded;
or a hydrate thereof.

19 Claims, 6 Drawing Sheets

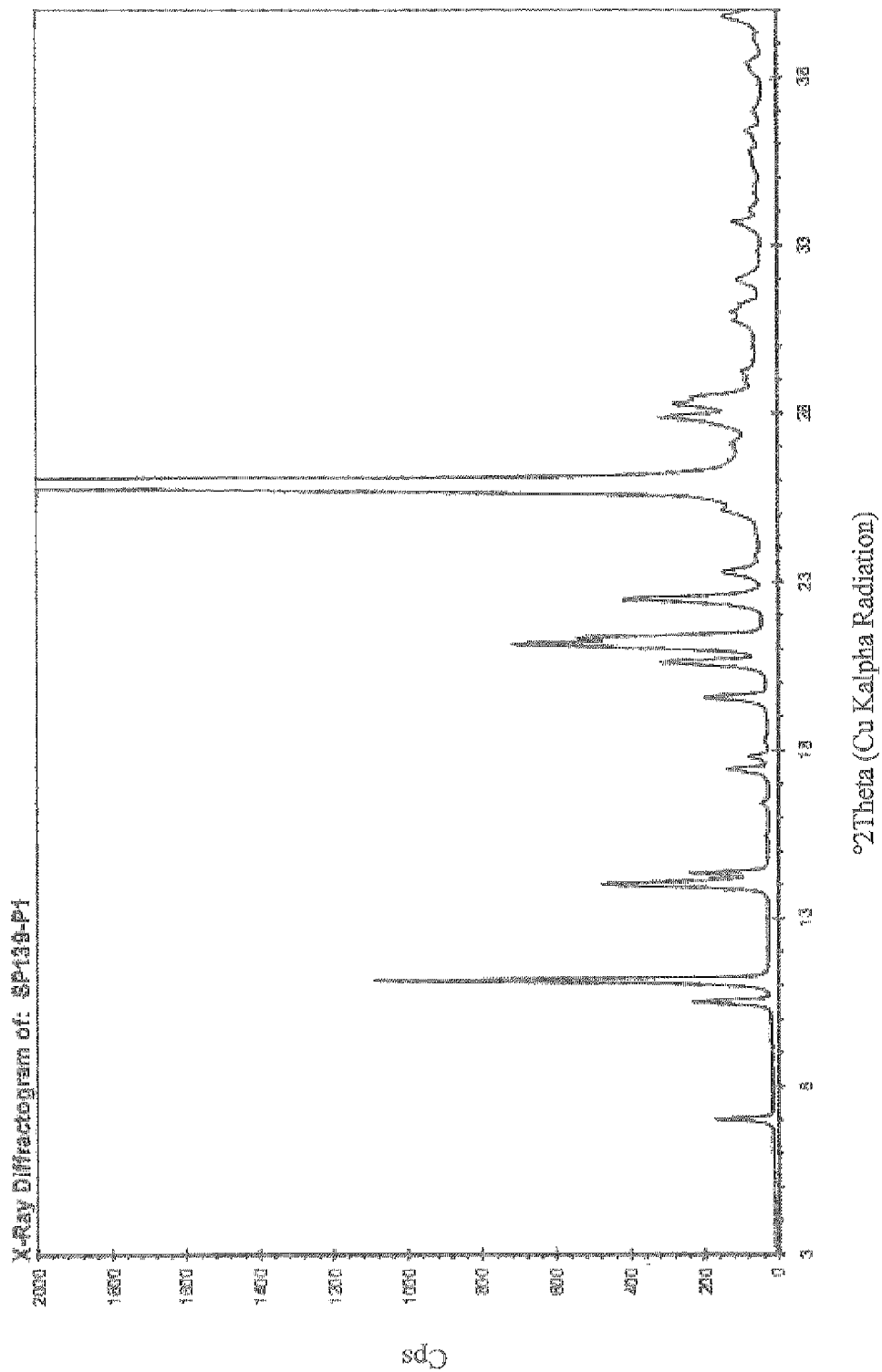

CALCIUM SALTS OF COMPOUNDS AS ANTI-INFLAMMATORY, IMMUNOMODULATORY AND ANTI-PROLIFERATORY AGENTS

This application claims the benefit of the filing date of U.S. Provisional Application Ser. No. 61/360,670 filed Jul. 1, 2010, which is incorporated by reference herein.

The present invention relates to novel calcium salts of compounds that can be used as antiinflammatory, immunomodulatory and antiproliferatory agents. In particular the invention refers to new calcium salts of compounds which inhibit dihydroorotate dehydrogenase (DHODH), a process for their manufacture, pharmaceutical compositions containing them and to their use for the treatment and prevention of diseases, in particular their use in diseases where there is an advantage in inhibiting dihydroorotate dehydrogenase (DHODH).

Rheumatoid arthritis (RA) is a disease which is quite common especially among elder people. Its treatment with usual medications as for example non-steroid anti-inflammatory agents is not satisfactory. In view of the increasing ageing of the population, especially in the developed Western countries or in Japan the development of new medications for the treatment of RA is urgently required.

WO 2003/006425 describes certain specific compounds which are reported to be useful for treatment and prevention of diseases where there is an advantage in inhibiting dihydroorotate dehydrogenase (DHODH). However, the specific salts according to the present invention are not disclosed.

WO 99/38846 and EP 0 646 578 disclose compounds which are reported to be useful for treatment of RA.

A medicament against rheumatoid arthritis with a new mechanism of action, leflunomide, was recently put on the market by the company Aventis under the tradename ARAVA [EP 780128, WO 97/34600]. Leflunomide has immunomodulatory as well as anti-inflammatory properties [EP 217206, DE 2524929]. The mechanism of action is based upon the inhibition of dihydroorotate dehydrogenase (DHODH), an enzyme of the pyrimidine biosynthesis.

De Julian-Ortiz (J. Med. Chem. 1999, 42, 3308-3314) describes certain potential Anti-Herpes compounds with cyclopentenoic acid moieties DE 33 46 814 A1 describes certain carbonic acid amide derivatives for the treatment, prevention and amelioration of diseases connected to cerebral dysfunction and symptoms caused thereby.

In the body, DHODH catalyzes the synthesis of pyrimidines, which are necessary for cell growth. An inhibition of DHODH inhibits the growth of (pathologically) fast proliferating cells, whereas cells which grow at normal speed may obtain their required pyrimidine bases from the normal metabolic cycle. The most important types of cells for the immuno response, the lymphocytes, use exclusively the synthesis of pyrimidines for their growth and react particularly sensitively to DHODH inhibition. Substances that inhibit the growth of lymphocytes are important medicaments for the treatment of auto-immuno diseases.

The DHODH inhibitor leflunomide (ARAVA) is the first medicament of this class of compounds (leflunomides) for the treatment of rheumatoid arthritis, WO 99/45926 is a further reference that discloses compounds which act as inhibitors of DHODH.

JP-A-50-121428 discloses N-substituted cyclopentene-1,2-dicarboxylic acid monoamides as herbicides and their syntheses. For example, N-(4-chlorophenyl)-1-cyclopentene-1,2-dicarboxylic acid monoamide is produced by reacting 1-cyclopentene-1,2-dicarboxylic anhydride with 4-chloroaniline.

In the Journal of Med. Chemistry, 1999, Vol. 42, pages 3308-3314, virtual combinatorial syntheses and computational screening of new potential Anti-Herpes compounds are described. In Table 3 on page 3313 experimental results regarding $IC_{50}$ and cytotoxicity are presented for 2-(2,3-difluorophenylcarbamoyl)-1-cyclopentene-1-carboxylic acid, 2-(2,6-difluorophenylcarbamoyl)-1-cyclopentene-1-carboxylic acid and 2-(2,3,4-trifluorophenyl-carbamoyl)-1-cyclopentene-1-carboxylic acid.

DE 3346814 and U.S. Pat. No. 4,661,630 disclose carboxylic acid amides. These compounds are useful for diseases attended with cerebral dysfunction and also have anti-ulcer, anti-asthma, anti-inflammatory and hypo-cholesterol activities.

In EP 0097056, JP 55157547, DE 2851379 and DE 2921002 tetrahydrophthalamic acid derivatives are described.

It is an object of the present invention to provide alternative effective agents, specifically in the form of their calcium salts, which can be used for the treatment of diseases which require the inhibition of DHODH.

Particularly, it has previously been found that compounds of the general formula (I) shown herein below, such as 2-(3-Fluoro-3'-methoxy-biphenyl-4-ylcarbamoyl)-cyclopent-1-enecarboxylic acid (INN Vidofludimus), exhibit good anti-inflammatory activity and their usability in the oral therapy for the treatment of autoimmune diseases such as for example rheumatoid arthritis or inflammatory bowel diseases had been addressed. However, the solubility of the aforementioned compounds in aqueous media is less than 1 mg/ml at neutral pH.

The solubility of a compound is an important characteristic in drug discovery, as it serves as a starting point for formulation development. Furthermore, after oral administration, the resorption of a drug from the intestines into the circulation is at least in part dependent on its solubility. Only dissolved substances can be resorbed, so that an increase in solubility can be expected to result in a better uptake of a compound in the gastrointestinal tract, i.e. a better oral bioavailability and hence improved pharmacokinetic properties. It is desirable to provide compounds having enhanced bioavailability in order to improve their use as pharmaceutical compound for oral application.

Therefore, the present inventors have undertaken efforts to increase the solubility of the compounds in aqueous media and consequently their bioavailability. With this motivation, a study to develop a novel salt form of the compounds was performed, resulting in salts which unexpectedly exhibit significantly improved physicochemical properties.

It has been found that the calcium salts of compounds of formula (I) as described herein below, such as the calcium salt of 2-(3-Fluoro-3'-methoxy-biphenyl-4-ylcarbamoyl)-cyclopent-1-enecarboxylic acid, exhibit favorable physicochemical properties such as improved aqueous solubility while maintaining good long-term stability. Furthermore, it was found that not all salts of the compound generally increase aqueous solubility to the same extent; in fact, although the solubilities of the tested salts are all higher than for the free acid, they significantly differ from each other. More importantly, the calcium salt surprisingly exhibits a markedly increased bioavailability, compared with other salts or the free acid.

Accordingly, a novel class of calcium salts of compounds with an inhibitory effect on DHODH, in particular human DHODH, was found.

The present invention is therefore directed to the calcium salts of compounds of the general formula (I)

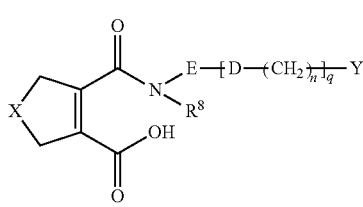

wherein
X is selected from the group consisting of $CH_2$, S, or O;
D is O or S;
$R^8$ is hydrogen or alkyl, preferably hydrogen or methyl;
E is an optionally substituted phenylene group;
Y is a monocyclic or bicyclic substituted or unsubstituted 6-9 membered ring system which may contain one or more heteroatoms selected from N or S and which contains at least one aromatic ring; preferably, Y is substituted or unsubstituted phenyl;
n is 0 or 1, preferably 0; and
q is 0 or 1, preferably 0;
with the proviso that compounds wherein q=0, Y=unsubstituted phenyl and E=unsubstituted phenylene are excluded;
or a hydrate thereof.

E is preferably an unsubstituted phenylene group or a phenylene group which is substituted with one or more groups independently selected from halogen, nitro or alkoxy; more preferably E is a phenylene group which is substituted with one fluorine or chlorine atom, one methoxy group or with four fluorine atoms. Even more preferably, E is a phenylene group which is substituted with one or four fluorine atoms, yet even more preferably one fluorine atom.

Y is preferably an optionally substituted phenyl, pyridine or benzothiophene group. More preferably, Y is an unsubstituted phenyl group or a phenyl group which is substituted with one or more groups independently selected from halogen, alkyl, alkoxy, haloalkoxy, haloalkyl or CN. Even more preferably E is a phenyl group which is substituted with one or more groups independently selected from fluorine, chlorine, CN, methoxy, ethoxy, trifluoromethyl or trifluoromethoxy. Yet even more preferably, E is a phenyl group which is substituted with one or more groups independently selected from methoxy or trifluoromethoxy, yet even more preferably methoxy.

An alkyl group, if not stated otherwise, is preferably a saturated linear or branched chain of 1 to 6 carbon atoms, preferably a methyl, ethyl, propyl, isopropyl, butyl, t-butyl, isobutyl, pentyl or hexyl group, a methyl, ethyl, isopropyl or t-butyl group being more preferred, a methyl or ethyl group being even more preferred, a methyl group being yet even more preferred.

An alkoxy group denotes an O-alkyl group, the alkyl group being as defined above.

A haloalkyl group denotes an alkyl group which is substituted by one or more halogen atoms, the alkyl group being as defined above; a trifluoromethyl being preferred.

A haloalkyloxy group denotes an alkoxy group which is substituted by one or halogen atoms, the alkoxy group being as defined above; a $OCF_3$ being preferred.

Halogen is preferably chlorine, bromine, fluorine or iodine, fluorine, chlorine or bromine being preferred, fluorine being more preferred.

The invention also provides a pharmaceutical composition comprising the calcium salts of the compounds of formula (I) as described above or, together with a pharmaceutically acceptable diluent or carrier therefore.

In another aspect, the present invention also provides a method for the treatment or prophylaxis of a condition where there is an advantage in inhibiting dihydroorotate dehydrogenase (DHODH) which comprises the administration of an effective amount of a calcium salt of the compounds of formula (I) as described above.

The invention is also directed to the use of a calcium salt of the compounds of formula (I) as described above for the production of a medicament for the prevention and treatment of diseases, where inhibition of the pyrimidine biosynthesis is of benefit.

The present invention also encompasses hydrates of the salts according to the present invention, which specifies that crystals obtainable from said salts contain water in specific stoichiometric or substoichiometric amounts, such as for example 0, 5, 1 or 2 water molecules per molecule of the compound of formula (I) or formula (Ia) as described herein, Further preferred aspects of the present invention are summarized in the following items [1] to [8]:

[1] A salt of the compound of the formula (Ia)

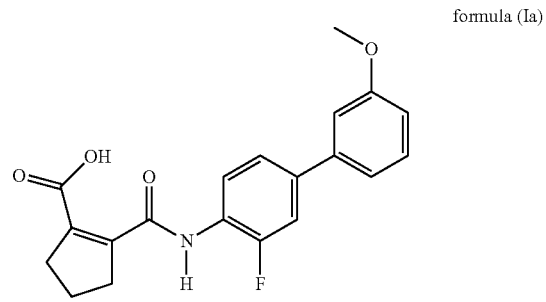 [SMILES: COc1cccc(-c2ccc(NC(=O)C3=C(C(=O)O)CCC3)c(F)c2)c1]

formula (Ia)

with a base selected from the group calcium (Ca), diethylamine (DEA), N-methyl-D-glucamine (NMG), lithium (Li), zinc (ZN), L-arginine, 4-(2-hydroxyethyl)morpholine (HEM), L-lysine (LYS), choline (CHO) and ammonia ($NH_3$).

[2] The compound of item [1], which is a salt of 2-(3-Fluoro-3'-methoxy-biphenyl-4-ylcarbamoyl)-cyclopent-1-en-ecarboxylic acid with any base selected from the group consisting of calcium (Ca), diethylamine (DEA), N-methyl-D-glutamine (NMG).

[3] A pharmaceutical composition comprising a compound as defined in any of items [1] to [2] together with pharmaceutically acceptable diluents or carriers.

[4] A compound according to items [1] to [2] for the use as a medicament.

[5] The use of the compound of the formula (Ia) as defined in any of items [1] to [2] in the manufacture of a medicament for use in treatment of a disease or a therapeutic indication in which inhibition of dihydroorotate dehydrogenase and/or Interleukin-17 (IL-17) is beneficial.

[6] The use of item [5], wherein the disease or indication is an autoimmune disease.

[7] The use of item [6], wherein the said autoimmune diseases are selected from the group consisting of ankylosing spondylitis, autoimmune thyroiditis, coeliac disease, Grave's disease, inflammatory bowel disease (Crohn's disease, ulcerative colitis), diabetes mellitus type 1, systemic lupus erythematosus, multiple sclerosis, vitiligo, osteoarthritis, psoriasis, psoriatic arthritis or rheumatoid arthritis.

[8] The use of the compound of the formula (Ia) as defined in any of items [1] to [2] in the manufacture of a medicament for use in treatment of any forms of neoplasms.

In addition, the present invention provides methods for preparing the compounds of the invention such as desired amides of the formula (I), as well as for the calcium salts thereof as described above.

A first method for synthesis of amides of formula (I) comprises the step of reacting an acid anhydride of formula (II) with an amine of the formula (III).

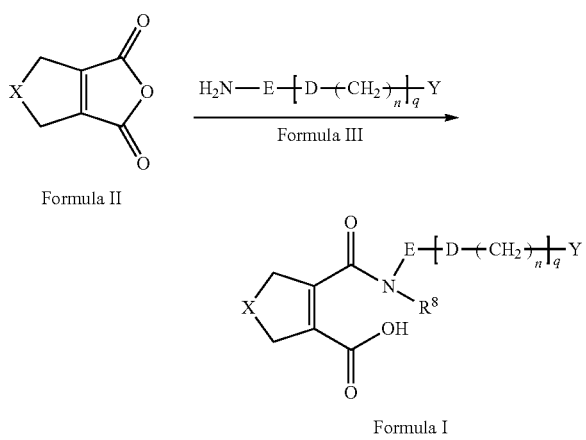

Formula II

Formula I

A second method of the invention for preparing the compounds of formula (I) comprises the step of reacting an amine of the formula (IV) with an aryl-boronic acid of the general formula (V) $(HO)_2B-E[D-(CHR^3)_n]_q—Y$ [M. P. Winters, Tetrahedron Lett, 39, (1998), 2933-2936].

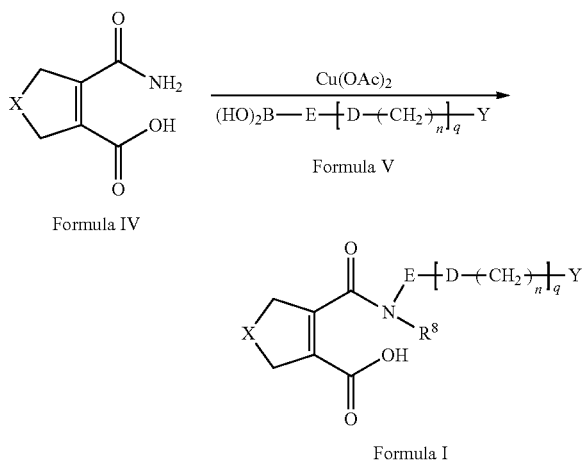

Formula IV

Formula I

A third method of the invention for preparing the compounds of formula (I) comprises the step of reacting an halogen derivative of the formula (VI) with an arylboronic acid of the general formula (VII) [N. E. Leadbeater, S. M. Resouly, Tetrahedron, 55, 1999, 11889-11894]. Q is a halogen group such as chlorine, bromine, fluorine or iodine, bromine being preferred.

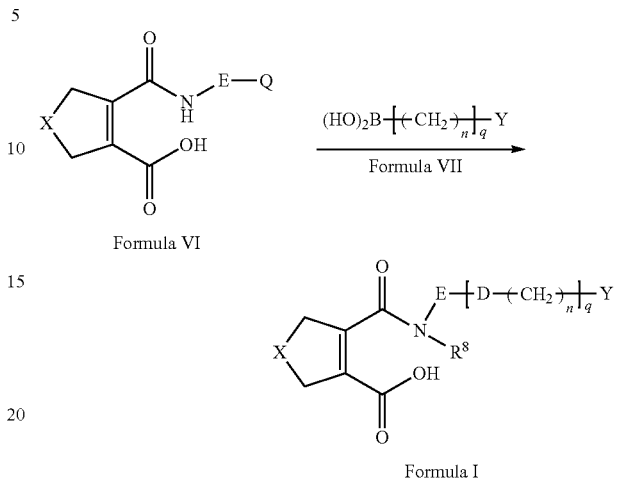

Formula VI

Formula I

In the structures of formulae II to VII as depicted herein, the residues X, E, D, Y, $R_8$, as well as the variables n and q have the meaning as defined herein for formula I.

Preferably, the salts of the present invention are the calcium salts derived from a compound selected from the group comprising the compounds 1 to 76 below:

1. 2-((4-(benzyloxy)phenyl)carbamoyl)cyclopent-1-enecarboxylic acid
13. 2-((2'-fluoro-[1,1'-biphenyl]-4-yl)carbamoyl)cyclopent-1-enecarboxylic acid
14. 2-((2'-chloro-[1,1'-biphenyl]-4-yl)carbamoyl)cyclopent-1-enecarboxylic acid
15. 2-((2'-methoxy-[1,1'-biphenyl]-4-yl)carbamoyl)cyclopent-1-enecarboxylic acid
16. 2-((4-((2,6-difluorobenzyl)oxy)phenyl)carbamoyl)cyclopent-1-enecarboxylic acid
17. 2-((2'-ethoxy-3-fluoro-[1,1'-biphenyl]-4-yl)carbamoyl)cyclopent-1-enecarboxylic acid
18. 2-((2-chloro-3'-cyano-[1,1'-biphenyl]-4-yl)carbamoyl)cyclopent-1-enecarboxylic acid
19. 2-((2-chloro-4'-methoxy-[1,1'-biphenyl]-4-yl)carbamoyl)cyclopent-1-enecarboxylic acid
22. 2-((3-chloro-4-(6-methoxypyridin-3-yl)phenyl)carbamoyl)cyclopent-1-enecarboxylic acid
23. 2-((4'-methoxy-2-methyl-[1,1'-biphenyl]-4-yl)carbamoyl)cyclopent-1-enecarboxylic acid
24. 2-((3,5-dibromo-4-(2,5-difluorobenzyl)oxy)phenyl)carbamoyl)cyclopent-1-enecarboxylic acid
25 2-((3,5-dibromo-4-((3,4-difluorobenzyl)oxy)phenyl)carbamoyl)cyclopent-1-enecarboxylic acid
26. 2-((3-fluoro-3'-methoxy-[1,1'-biphenyl]-4-yl)carbamoyl)cyclopent-1-enecarboxylic acid
27. 2-((3,3'-difluoro-[1,1'-biphenyl]-4-yl)carbamoyl)cyclopent-1-enecarboxylic acid
29. 4-((4-(benzyloxy)-3,5-dibromophenyl)carbamoyl)-2,5-dihydrothiophene-3-carboxylic acid
30. 2-((3,4',5-trifluoro-3'-methyl-[1,1'-biphenyl]-4-yl)carbamoyl)cyclopent-1-enecarboxylic acid
31. 2-((3,5-difluoro-2'-methoxy-[1,1'-biphenyl]-4-yl)carbamoyl)cyclopent-1-enecarboxylic acid
32. 2-((2'-methoxy-3-nitro-[1,1'-biphenyl]-4-yl)carbamoyl)cyclopent-1-enecarboxylic acid 33. 2-((3-methoxy-[1,1'-biphenyl]-4-yl)carbamoyl)cyclopent-1-enecarboxylic acid
34. 2-((2'-chloro-3-methoxy-[1,1'-biphenyl]-4-yl)carbamoyl)cyclopent-1-enecarboxylic acid
35. 2-((3-methoxy-3'-(trifluoromethoxy)-[1,1'-biphenyl]-4-yl)carbamoyl)cyclopent-1-enecarboxylic acid
36. 2-((2'-fluoro-3-methoxy-[1,1'-biphenyl]-4-yl)carbamoyl)cyclopent-1-enecarboxylic acid
37. 2-((2',3,4'-trimethoxy-[1,1'-biphenyl]-4-yl)carbamoyl)cyclopent-1-enecarboxylic acid
38. 2-((3'-ethoxy-3-methoxy-[1,1'-biphenyl]-4-yl)carbamoyl)cyclopent-1-enecarboxylic acid
39. 2-((3,3'-dimethoxy-[1,1'-biphenyl]-4-yl)carbamoyl)cyclopent-1-enecarboxylic acid
40. 2-((3,5-dibromo-4-(2-chloro-6-fluorobenzyl)oxy)phenyl)carbamoyl)cyclopent-1-enecarboxylic acid
41. 4-((2'-chloro-[1,1'-biphenyl]-4-yl)carbamoyl)-2,5-dihydrothiophene-3-carboxylic acid
42. 2-((4-(m-tolylthio)phenyl)carbamoyl)cyclopent-1-enecarboxylic acid
43. 2-((3'-(trifluoromethoxy)-[1,1'-biphenyl]-4-yl)carbamoyl)cyclopent-1-enecarboxylic acid
44. 2-((4-(benzo[b]thiophen-2-yl)phenyl)carbamoyl)cyclopent-1-enecarboxylic acid
45. 2-((4-(benzo[b]thiophen-2-yl)-2-fluorophenyl)carbamoyl)cyclopent-1-enecarboxylic acid
46. 2-((3'-ethoxy-3-fluoro-[1,1'-biphenyl]-4-yl)carbamoyl)cyclopent-1-enecarboxylic acid
47. 4-((3,5-difluoro-2'-methoxy-[1,1'-biphenyl]-4-yl)carbamoyl)-2,5-dihydrofuran-3-carboxylic acid
50. 2-((4-phenoxyphenyl)carbamoyl)cyclopent-1-enecarboxylic acid
52. 4-((3,5-dibromo-4-(2-chloro-6-fluorobenzyl)oxy)phenyl)carbamoyl)-2,5-dihydrothiophene-3-carboxylic acid
53. 2-((3-chloro-2'-methoxy-[1,1'-biphenyl]-4-yl)carbamoyl)cyclopent-1-enecarboxylic acid
54. 2-((2-chloro-2'-methoxy-[1,1'-biphenyl]-4-yl)carbamoyl)cyclopent-1-enecarboxylic acid
56. 2-((2,3,5,6-tetrafluoro-2'-methoxy-[1,1'-biphenyl]-4-yl)carbamoyl)cyclopent-1-enecarboxylic acid
57. 2-((2'-methoxy-3-methyl-[1,1'-biphenyl]-4-yl)carbamoyl)cyclopent-1-enecarboxylic acid
58. 2-((3,5-dichloro-2'-methoxy-[1,1'-biphenyl]-4-yl)carbamoyl)cyclopent-1-enecarboxylic acid
62. 2-((2'-ethoxy-3,5-difluoro-[1,1'-biphenyl]-4-yl)carbamoyl)cyclopent-1-enecarboxylic acid
63. 2-((3'-ethoxy-3,5-difluoro-[1,1'-biphenyl]-4-yl)carbamoyl)cyclopent-1-enecarboxylic acid
64. 2-((3,5-difluoro-3'-(trifluoromethoxy)-[1,1'-biphenyl]-4-yl)carbamoyl)cyclopent-1-enecarboxylic acid
65. 2-((2'-chloro-3,5-difluoro-[1,1'-biphenyl]-4-yl)carbamoyl)cyclopent-1-enecarboxylic acid
66. 2-((2',3,5-trifluoro-[1,1'-biphenyl]-4-yl)carbamoyl)cyclopent-1-enecarboxylic acid
67. 2-((3,5-difluoro-2',4'-dimethoxy-[1,1'-biphenyl]-4-yl)carbamoyl)cyclopent-1-enecarboxylic acid
68. 2-((3-chloro-4-((2-trifluoromethyl)benzyl)oxy)phenyl)carbamoyl)cyclopent-1-enecarboxylic acid
69. 2-((3-chloro-4-(2-chloro-6-fluorobenzyl)oxy)phenyl)carbamoyl)cyclopent-1-enecarboxylic acid
72. 2-((4-benzyloxy)-3-chlorophenyl)carbamoyl)cyclopent-1-enecarboxylic acid
74. 2-((3-chloro-4-((2-fluorobenzyl)oxy)phenyl)carbamoyl)cyclopent-1-enecarboxylic acid
76. 2-((3-fluoro-2'-methoxy-[1,1'-biphenyl]-4-yl)oxy)carbonyl)cyclopent-1-enecarboxylic acid Preferably, the calcium salts of the present invention are the abovementioned calcium salts, wherein the compound of formula (I) is selected from the group comprising the compounds shown below in table 1:

TABLE 1

| N | Structure | $^1$H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 01 | 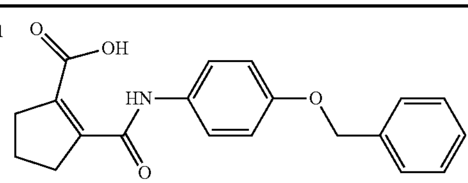 | N.D. | 337.37 | 338 [M + H]$^+$ | 0.350 | 8.2 | N.D. |
| 13 | 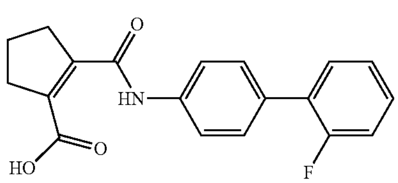 [SMILES: O=C(O)C1=C(C(=O)Nc2ccc(-c3ccccc3F)cc2)CCC1] | δ = 1.91 (m$_C$, 2H, CH$_2$), 2.65 (m$_C$, 2H, CH$_2$), 2.78 (m$_C$, 2H, CH$_2$), 7.27-7.51 (m, 6H, CH$_{Ar}$), 7.72 (d, 2H, CH$_{Ar}$), 10.40 (s, 1H, NH), 12.67 (s, 1H, OH). | 325 | 326 [M + H]$^+$ | A | C | C |
| 14 | 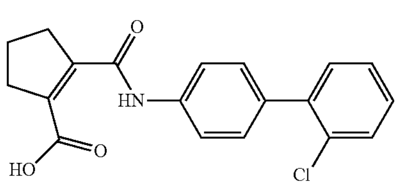 [SMILES: O=C(O)C1=C(C(=O)Nc2ccc(-c3ccccc3Cl)cc2)CCC1] | δ = 1.95 (m$_C$, 2H, CH$_2$), 2.65 (m$_C$, 2H, CH$_2$), 2.78 (m$_C$, 2H, CH$_2$), 7.35-7.72 (m, 8H, CH$_{Ar}$), 10.36 (s, 1H, NH), 12.66 (s, 1H, OH). | 341 | 342 [M + H]$^+$ | A | C | C |

TABLE 1-continued

| N | Structure | $^1$H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 15 | 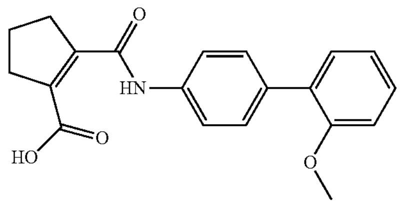 [SMILES: COc1ccccc1-c1ccc(NC(=O)C2=C(C(=O)O)CCC2)cc1] | δ = 1.94 (m$_C$, 2H, CH$_2$), 2.66 (m$_C$, 2H, CH$_2$), 2.79 (m$_C$, 2H, CH$_2$), 3.76 (s, 3H, O—CH$_3$), 7.01-7.67 (m, 8H, CH$_{Ar}$), 10.30 (s, 1H, NH). | 337 | 338 [M + H]$^+$ | A | N.D. | N.D. |
| 16 | 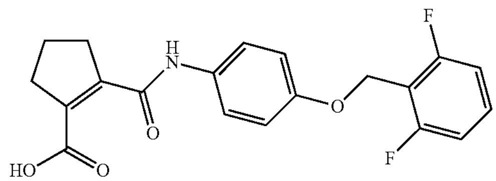 [SMILES: O=C(O)C1=C(C(=O)Nc2ccc(OCc3c(F)cccc3F)cc2)CCC1] | δ = 1.90 (m$_C$, 2H, CH$_2$), 2.57 (m$_C$, 2H, CH$_2$), 2.76 (m$_C$, 2H, CH$_2$), 5.08 (s, 2H, CH$_2$—O), 6.95-7.57 (m, 7H, CH$_{Ar}$), 10.11 (s, 1H, NH), 11.33 (s, 1H, OH). | 373 | 374 [M + H]$^+$ | A | N.D. | N.D. |
| 17 | 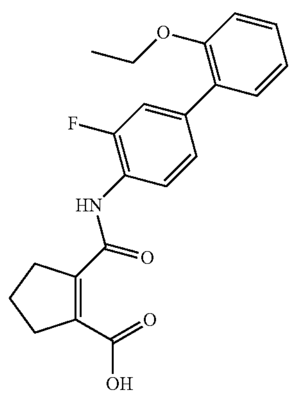 [SMILES: CCOc1ccccc1-c1ccc(NC(=O)C2=C(C(=O)O)CCC2)c(F)c1] | δ = 1.04 (m$_C$, 3H, O—CH$_2$—CH$_3$), 1.65 (m$_C$, 2H, CH$_2$), 2.45 (m$_C$, 2H, CH$_2$), 2.55 (m$_C$, 2H, CH$_2$), 3.82 (m$_C$, 2H, O—CH$_2$—CH$_3$), 6.75-6.87 (m, 2H, CH$_{Ar}$), 7.06-7.28 (m, 4H, CH$_{Ar}$), 7.71-7.77 (m, 1H, CH$_{Ar}$), 10.23 (s, 1H, NH), 12.83 (s, 1H, OH). | 369 | 370 [M + H]$^+$ | A | N.D. | N.D. |
| 18 | 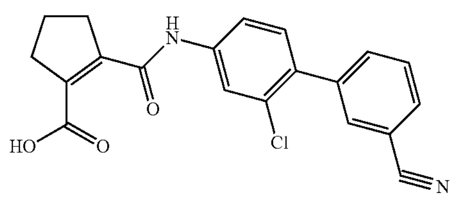 [SMILES: N#Cc1cccc(-c2ccc(NC(=O)C3=C(C(=O)O)CCC3)cc2Cl)c1] | δ = 1.7 (m$_C$, 2H, CH$_2$), 2.60 (m$_C$, 2H, CH$_2$), 2.73 (m$_C$, 2H, CH$_2$), 7.36-7.91 (m, 7H, CH$_{Ar}$), 10.61 (s, 1H, NH), 12.61 (s, 1H, OH). | 366 | 367 [M + H]$^+$ | A | N.D. | N.D. |
| 19 | 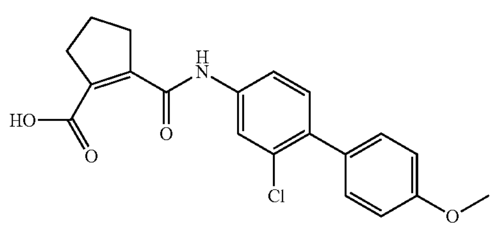 [SMILES: COc1ccc(-c2ccc(NC(=O)C3=C(C(=O)O)CCC3)cc2Cl)cc1] | δ = 2.16 (m$_C$, 2H, CH$_2$), 2.89 (m$_C$, 2H, CH$_2$), 3.01 (m$_C$, 2H, CH$_2$), 4.03 (s, 3H, O—CH$_3$), 7.23-8.15 (m, 7H, CH$_{Ar}$), 10.66 (s, 1H, NH), 13.00 (s, 1H, OH). | 371 | 372 [M + H]$^+$ | A | A | A |
| 22 | 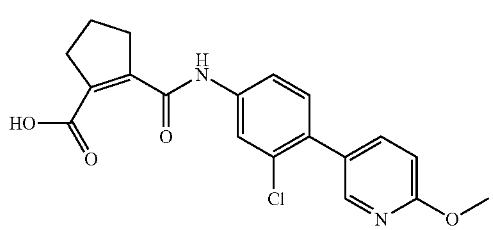 [SMILES: COc1ccc(-c2ccc(NC(=O)C3=C(C(=O)O)CCC3)cc2Cl)cn1] | δ = 1.74 (m$_C$, 2H, CH$_2$), 2.48 (m$_C$, 2H, CH$_2$), 3.71 (s, 3H, O—CH$_3$), 6.70-8.02 (m, 6H, CH$_{Ar}$), 10.28 (s, 1H, NH), 12.48 (s, 1H, OH). | 372 | 373 [M + H]$^+$ | A | N.D. | N.D. |

TABLE 1-continued

| N | Structure | ¹H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 23 | 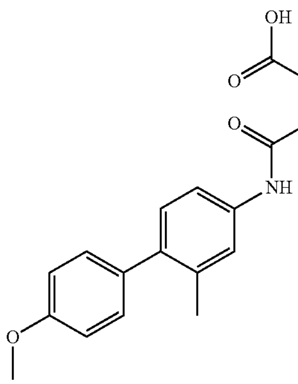 | δ = 1.92 (m$_C$, 2H, CH$_2$), 2.50 (s, 3H, CH$_3$), 2.66 (m$_C$, 2H, CH$_2$), 2.79 (m$_C$, 2H, CH$_2$), 3.79 (s, 3H, O—CH$_3$), 6.97-7.54 (m, 7H, CH$_{Ar}$), 10.20 (s, 1H, NH), 12.00 (s, 1H, OH). | 351 | 352 [M + H]$^+$ | A | N.D. | N.D. |
| 24 | 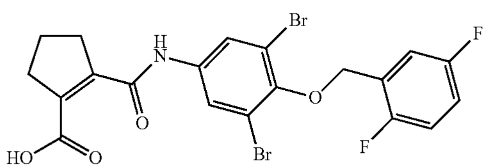 [SMILES: O=C(O)C1=C(C(=O)Nc2cc(Br)c(OCc3cc(F)ccc3F)c(Br)c2)CCC1] | δ = 1.92 (m$_C$, 2H, CH$_2$), 2.64 (m$_C$, 2H, CH$_2$), 2.74 (m$_C$, 2H, CH$_2$), 5.02 (s, 2H, O—CH$_2$), 7.28-7.93 (m, 5H, CH$_{Ar}$), 10.41 (s, 1H, NH), 12.68 (s, 1H, OH). | 529 | 530 [M + H]$^+$ | A | B | C |
| 25 | 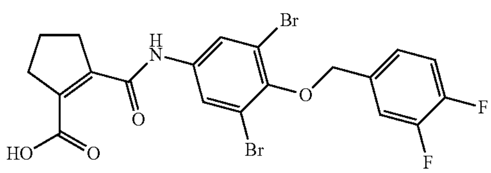 [SMILES: O=C(O)C1=C(C(=O)Nc2cc(Br)c(OCc3ccc(F)c(F)c3)c(Br)c2)CCC1] | δ = 1.83 (m$_C$, 2H, CH$_2$), 2.55 (m$_C$, 2H, CH$_2$), 2.65 (m$_C$, 2H, CH$_2$), 4.86 (s, 2H, O—CH$_2$), 7.28-7.85 (m, 5H, CH$_{Ar}$), 10.34 (s, 1H, NH), 12.56 (s, 1H, OH). | 529 | 530 [M + H]$^+$ | A | N.D. | N.D. |
| 26 | 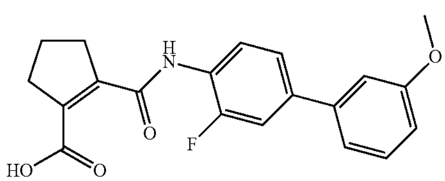 [SMILES: COc1cccc(-c2ccc(NC(=O)C3=C(C(=O)O)CCC3)c(F)c2)c1] | δ = 1.89 (m$_C$, 2H, CH$_2$), 2.69 (m$_C$, 2H, CH$_2$), 2.80 (m$_C$, 2H, CH$_2$), 3.83 (s, 3H, O—CH$_3$), 6.92-8.09 (m, 7H, CH$_{Ar}$), 10.57 (s, 1H, NH). | 355 | 356 [M + H]$^+$ | A | C | C |
| 27 | 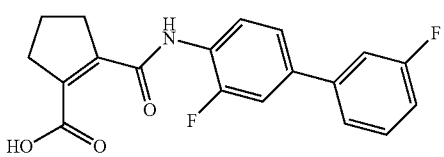 [SMILES: O=C(O)C1=C(C(=O)Nc2ccc(-c3cccc(F)c3)cc2F)CCC1] | δ = 1.67 (m$_C$, 2H, CH$_2$), 2.47 (m$_C$, 2H, CH$_2$), 2.58 (m$_C$, 2H, CH$_2$), 6.94-7.91 (m, 7H, CH$_{Ar}$), 10.40 (s, 1H, NH), 12.81 (s, 1H, OH). | 343 | 344 [M + H]$^+$ | A | C | N.D. |
| 29 | 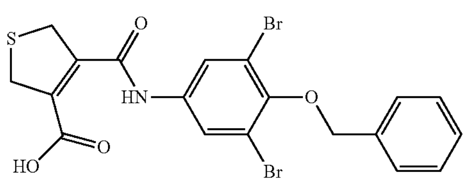 [SMILES: O=C(O)C1=C(C(=O)Nc2cc(Br)c(OCc3ccccc3)c(Br)c2)CSC1] | δ = 3.93 (m$_C$, 2H, CH$_2$), 4.03 (m$_C$, 2H, CH$_2$), 4.87 (s, 2H, O—CH$_3$), 7.30-7.83 (m, 7H, CH$_{Ar}$), 10.49 (s, 1H, OH). | 511 | 512 [M + H]$^+$ | A | C | B |
| 30 | 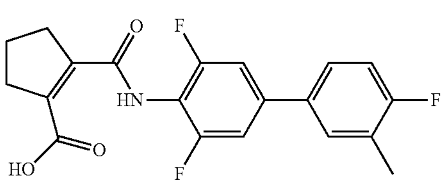 [SMILES: Cc1cc(-c2cc(F)c(NC(=O)C3=C(C(=O)O)CCC3)c(F)c2)ccc1F] | δ(CD3OD) = 1.91 (mC, 2H, CH2), 2.32 (s, 3H, CH3), 2.84 (mC, 2H, CH2), 2.93 (mC, 2H, CH2), 7.11 (mC, 1H, CHAr), 7.29 (s, 1H, CHAr), 7.32 (s, 1H, CHAr), 7.43-7.56 (m, 2H, CHAr). | 375 | 376 [M + H]+ | A | N.D. | N.D. |

TABLE 1-continued

| N | Structure | ¹H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 31 | 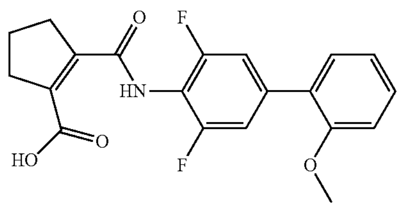 [SMILES: COc1ccccc1-c1cc(F)c(NC(=O)C2=C(C(=O)O)CCC2)c(F)c1] | δ(CD3OD) = 2.00 (mC, 2H, CH2), 2.84 (mC, 2H, CH2), 2.94 (mC, 2H, CH2), 3.83 (s, 3H, O—CH3), 7.00-7.10 (m, 2H, CHAr), 7.18 (s, 1H, CHAr), 7.21 (s, 1H, CHAr), 7.31-7.39 (m, 2H, CHAr). | 373 | 374 [M + H]+ | A | N.D. | N.D. |
| 32 | 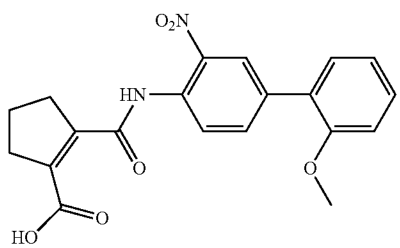 [SMILES: COc1ccccc1-c1ccc(NC(=O)C2=C(C(=O)O)CCC2)c([N+](=O)[O-])c1] | δ = 1.90 (mC, 2H, CH2), 2.64 (mC, 2H, CH2), 2.74 (mC, 2H, CH2), 3.76 (s, 3H, O—CH3), 7.03 (mC, 1H, CHAr), 7.11 (mC, 1H, CHAr), 7.34 (s, 1H, CHAr), 7.36 (s, 1H, CHAr), 7.72-7.82 (m, 2H, CHAr), 8.02 (s, 1H, CHAr), 10.59 (s, 1H, NH), 12.85 (s, 1H, OH). | 382 | 383 [M + H]+ | A | N.D. | N.D. |
| 33 | 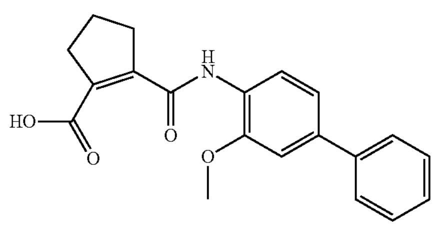 [SMILES: COc1cc(-c2ccccc2)ccc1NC(=O)C1=C(C(=O)O)CCC1] | δ = 1.85 (mC, 2H, CH2), 2.71 (mC, 2H, CH2), 2.80 (mC, 2H, CH2), 3.92 (s, 3H, O—CH3), 7.22 (mC, 1H, CHAr), 7.29-7.36 (m, 2H, CHAr), 7.45 (mC, 2H, CHAr), 7.67-7.71 (m, 2H, CHAr), 8.18 (mC, 1H, CHAr), 10.17 (s, 1H, NH). | 337 | 338 [M + H]+ | A | N.D. | N.D. |
| 34 | 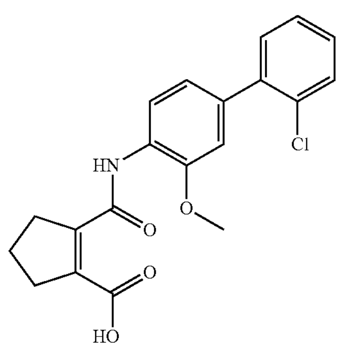 [SMILES: COc1cc(-c2ccccc2Cl)ccc1NC(=O)C1=C(C(=O)O)CCC1] | δ = 1.85 (mC, 2H, CH2), 2.71 (mC, 2H, CH2), 2.80 (mC, 2H, CH2), 3.85 (s, 3H, O—CH3), 6.98 (mC, 1H, CHAr), 7.10 (mC, 1H, CHAr), 7.37-7.46 (m, 3H, CHAr), 7.55 (mC, 1H, CHAr), 8.17 (mC, 1H, CHAr), 10.19 (s, 1H, NH). | 371 | 372 [M + H]+ | A | N.D. | N.D. |
| 35 | 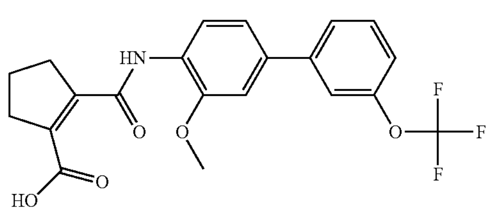 [SMILES: COc1cc(-c2cccc(OC(F)(F)F)c2)ccc1NC(=O)C1=C(C(=O)O)CCC1] | δ = 1.84 (mC, 2H, CH2), 2.71 (mC, 2H, CH2), 2.80 (mC, 2H, CH2), 3.93 (s, 3H, O—CH3), 7.26-7.35 (m, 3H, CHAr), 7.57 (mC, 1H, CHAr), 7.67 (s, 1H, CHAr), 7.74 (mC, 1H, CHAr), 8.23 (mC, 1H, CHAr), 10.33 (s, 1H, NH). | 421 | 422 [M + H]+ | A | N.D. | N.D. |

TABLE 1-continued

| N | Structure | ¹H-NMR | Molecule-Mass [g/mol] | HPLC/MS (ESI) | human IC$_{50}$-Value [µM] | murine IC$_{50}$-Value [µM] | rate IC$_{50}$-Value [µM] |
|---|---|---|---|---|---|---|---|
| 36 | 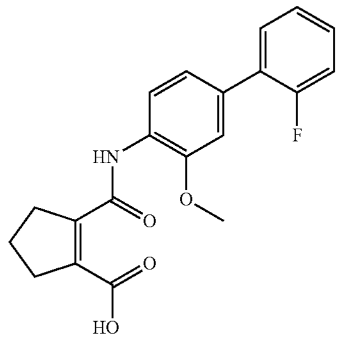 [SMILES: COc1cc(-c2ccccc2F)ccc1NC(=O)C1=C(C(=O)O)CCC1] | δ = 1.85 (mC, 2H, CH2), 2.71 (mC, 2H, CH2), 2.80 (mC, 2H, CH2), 3.88 (s, 3H, O—CH3), 7.11 (mC, 1H, CHAr), 7.19 (s, 1H, CHAr), 7.25-7.42 (mC, 3H, CHAr), 7.56 (mC, 1H, CHAr), 8.20 (mC, 1H, CHAr), 10.23 (s, 1H, NH). | 355 | 356 [M + H]+ | A | N.D. | N.D. |
| 37 | 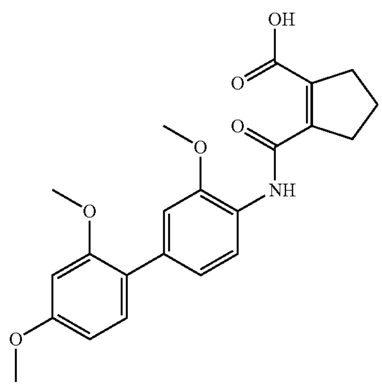 [SMILES: COc1ccc(-c2ccc(NC(=O)C3=C(C(=O)O)CCC3)c(OC)c2)c(OC)c1] | δ = 1.84 (mC, 2H, CH2), 2.71 (mC, 2H, CH2), 2.79 (mC, 2H, CH2), 3.76 (s, 3H, O—CH3), 3.79 (s, 3H, O—CH3), 3.83 (s, 3H, O—CH3), 6.60 (mC, 1H, CHAr), 6.64 (mC, 1H, CHAr), 7.98 (mC, 1H, CHAr), 7.08 (mC, 1H, CHAr), 7.24 (mC, 1H, CHAr), 8.04 (mC, 1H, CHAr), 10.24 (s, 1H, NH). | 397 | 398 [M + H]+ | A | N.D. | N.D. |
| 38 | 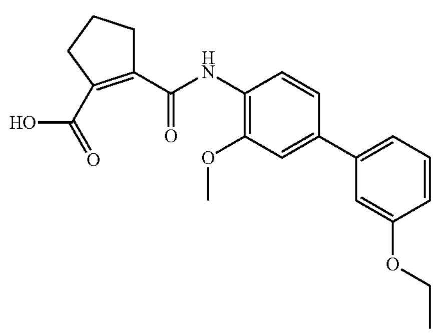 [SMILES: CCOc1cccc(-c2ccc(NC(=O)C3=C(C(=O)O)CCC3)c(OC)c2)c1] | δ = 1.34 (mC, 3H, O—CH2CH3), 1.84 (mC, 2H, CH2), 2.71 (mC, 2H, CH2), 2.80 (mC, 2H, CH2), 3.92 (s, 3H, O—CH3), 4.09 (mC, 2H, O—CH2CH3), 6.90 (mC, 1H, CHAr), 7.18-7.24 (mC, 3H, CHAr), 7.28 (mC, 1H, CHAr), 7.34 (mC, 1H, CHAr), 8.17 (mC, 1H, CHAr), 10.20 (s, 1H, NH). | 381 | 382 [M + H]+ | A | N.D. | N.D. |
| 39 | 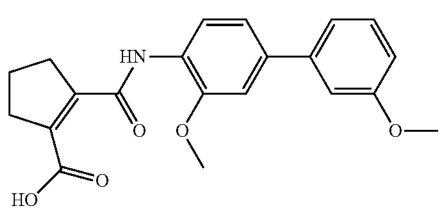 [SMILES: COc1cccc(-c2ccc(NC(=O)C3=C(C(=O)O)CCC3)c(OC)c2)c1] | δ = 1.84 (mC, 2H, CH2), 2.71 (mC, 2H, CH2), 2.80 (mC, 2H, CH2), 3.82 (s, 3H, O—CH3), 3.92 (s, 3H, O—CH3), 6.92 (mC, 1H, CHAr), 7.20-7.26 (m, 3H, CHAr), 7.28 (mC, 1H, CHAr), 7.36 (mC, 1H, CHAr), 8.19 (mC, 1H, CHAr), 10.24 (s, 1H, NH). | 367 | 368 [M + H]+ | A | N.D. | N.D. |
| 40 | 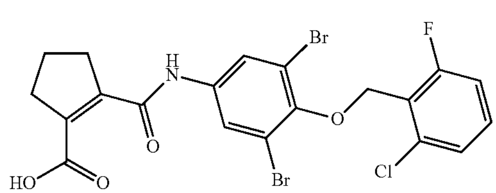 [SMILES: O=C(O)C1=C(C(=O)Nc2cc(Br)c(OCc3c(F)cccc3Cl)c(Br)c2)CCC1] | δ = 1.91 (mC, 2H, CH2), 2.63 (mC, 2H, CH2), 2.74 (mC, 2H, CH2), 5.21 (s, 2H, O—CH2), 7.22-7.89 (m, 5H, CHAr), 10.38 (s, 1H, NH), 12.65 (s, 1H, OH). | 545 | 546 [M + H]+ | A | C | C |

TABLE 1-continued

| N | Structure | ¹H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 41 | 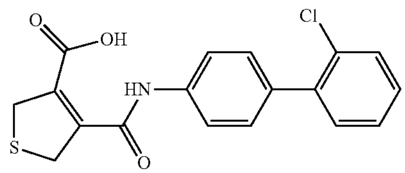 [SMILES: O=C(O)C1=C(C(=O)Nc2ccc(-c3ccccc3Cl)cc2)CSC1] | δ = 4.22 (mC, 2H, CH2), 4.34 (mC, 2H, CH2), 7.57-7.90 (m, 8H, CHAr), 10.65 (s, 1H, OH). | 359 | 360 [M + H]+ | A | C | C |
| 42 | 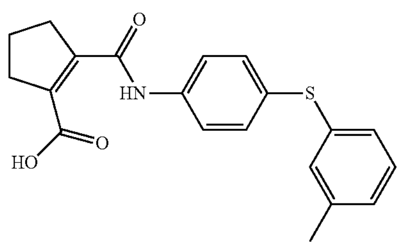 [SMILES: Cc1cccc(Sc2ccc(NC(=O)C3=C(C(=O)O)CCC3)cc2)c1] | δ 1.85 (mC, 2H, CH2), 2.17 (s, 2H, CH3), 2.56 (mC, 2H, CH2), 2.65-2.70 (m, 2H, CH2), 6.89-7.59 (m, 8H, CHAr), 10.29 (s, 1H, NH), 12.55 (s, 1H, OH). | 353 | 354 [M + H]+ | A | A | A |
| 43 | 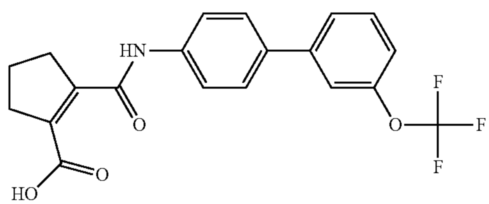 [SMILES: O=C(O)C1=C(C(=O)Nc2ccc(-c3cccc(OC(F)(F)F)c3)cc2)CCC1] | δ = 1.94 (mC, 2H, CH2), 2.66 (mC, 2H, CH2), 2.79 (mC, 2H, CH2), 7.25-7.76 (m, 8H, CHAr), 10.36 (s, 1H, NH). | 391 | 392 [M + H]+ | A | N.D. | N.D. |
| 44 | 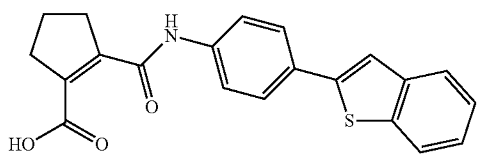 [SMILES: O=C(O)C1=C(C(=O)Nc2ccc(-c3cc4ccccc4s3)cc2)CCC1] | δ = 2.03 (mC, 2H, CH2), 2.77 (mC, 2H, CH2), 2.88 (mC, 2H, CH2), 7.41-8.07 (m, 9H, CHAr), 10.55 (s, 1H, NH), 12.83 (s, 1H, OH). | 363 | 364 [M + H]+ | A | N.D. | N.D. |
| 45 | 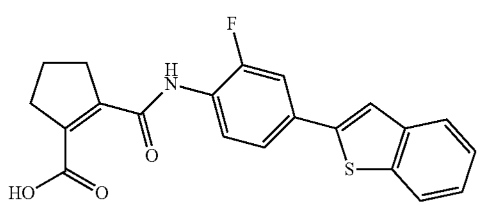 [SMILES: O=C(O)C1=C(C(=O)Nc2ccc(-c3cc4ccccc4s3)cc2F)CCC1] | δ = 1.74 (mC, 2H, CH2), 2.55 (mC, 2H, CH2), 2.64 (mC, 2H, CH2), 7.18-8.02 (m, 8H, CHAr), 10.55 (s, 1H, NH), 12.91 (s, 1H, OH). | 381 | 382 [M + H]+ | A | N.D. | N.D. |
| 46 | 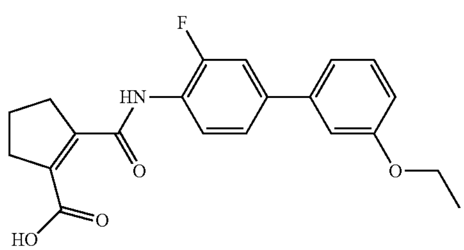 [SMILES: CCOc1cccc(-c2ccc(NC(=O)C3=C(C(=O)O)CCC3)c(F)c2)c1] | δ = 1.19 (s, 3H, O—CH2—CH3), 1.74 (mC, 2H, CH2), 2.54 (mC, 2H, CH2), 2.65 (mC, 2H, CH2), 3.95 (mC, 2H, O—CH2—CH3), 6.75-6.78 (m, 1H, CHAr), 7.04-7.38 (m, 3H, CHAr), 7.43-7.48 (m, 2H, CHAr), 7.87-7.93 (m, 1H, CHAr), 10.41 (s, 1H, NH), 12.90 (s, 1H, OH). | 369 | 370 [M + H]+ | A | C | C |
| 47 | 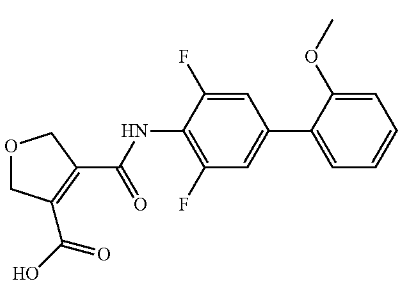 [SMILES: COc1ccccc1-c1cc(F)c(NC(=O)C2=C(C(=O)O)COC2)c(F)c1] | δ = 4.00 (s, 3H, O—CH3), 5.10-5.17 (m, 4H, CH2), 7.25-7.60 (m, 6H, CHAr), 10.55 (s, 1H, NH). | 375 | 376 [M + H]+ | A | C | A |

TABLE 1-continued

| N | Structure | ¹H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 50 | 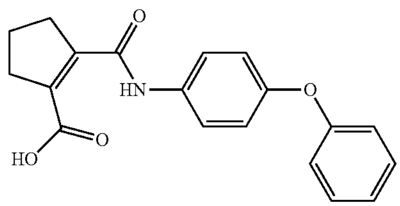 [SMILES: O=C(O)C1=C(C(=O)Nc2ccc(Oc3ccccc3)cc2)CCC1] | δ = 1.90 (mC, 2H, CH2), 2.64 (mC, 2H, CH2), 2.76 (mC, 2H, CH2), 6.94-7.64 (m, 9H, CHAr), 10.25 (s, 1H, NH), 12.73 (s, 1H, OH). | 323 | 324 [M + H]+ | A | A | A |
| 52 | 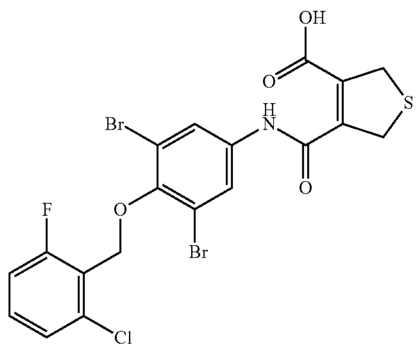 [SMILES: O=C(O)C1=C(C(=O)Nc2cc(Br)c(OCc3c(F)cccc3Cl)c(Br)c2)CSC1] | δ = 4.08 (mC, 4H, CH2), 5.21 (mC, 2H, CH2), 6.61-7.63 (m, 9H, CHAr), 11.24 (s, 1H, NH). | 563 | 564 [M + H]+ | A | B | A |
| 53 | 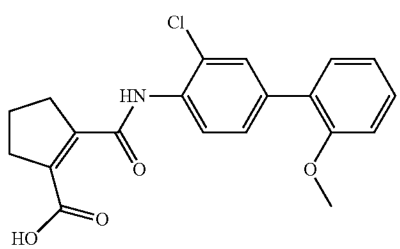 [SMILES: COc1ccccc1-c1ccc(NC(=O)C2=C(C(=O)O)CCC2)c(Cl)c1] | δ (CDCl3) = 2.03 (mC, 2H, CH2), 3.01-3.09 (m, 4H, CH2), 3.81 (s, 3H, O—CH3), 6.96-7.05 (m, 2H, CHAr), 7.26-7.37 (m, 2H, CHAr), 7.50 (mC, 1H, CHAr), 7.63 (s, 1H, CHAr), 8.36-8.39 (m, 2H, NH and CHAr). | 371 | 372 [M + H]+ | A | B | B |
| 54 | 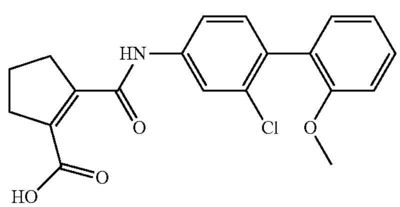 [SMILES: COc1ccccc1-c1ccc(NC(=O)C2=C(C(=O)O)CCC2)cc1Cl] | δ (CD3OD) = 2.00 (mC, 2H, CH2), 2.81 (mC, 2H, CH2), 2.9 (mC, 2H, CH2), 3.76 (s, 3H, O—CH3), 6.97-7.07 (m, 2H, CHAr), 7.14 (mC, 1H, CHAr), 7.22 (mC, 1H, CHAr), 7.37 (mC, 1H, CHAr), 7.50 (mC, 1H, CHAr), 7.85 (mC, 1H, CHAr). | 371 | 372 [M + H]+ | A | B | A |
| 56 | 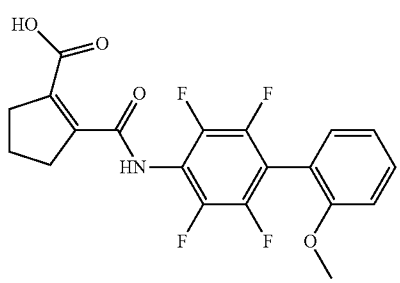 [SMILES: COc1ccccc1-c1c(F)c(F)c(NC(=O)C2=C(C(=O)O)CCC2)c(F)c1F] | δ (DMSO-d6) = 1.93 (mC, 2H, CH2), 2.67 (mC, 2H, CH2), 2.79 (mC, 2H, CH2), 3.79 (s, 3H, O—CH3), 7.09 (mC, 1H, CHAr), 7.20 (mC, 1H, CHAr), 7.37 (mC, 1H, CHAr), 7.51 (mC, 1H, CHAr). | 409 | 410 [M + H]+ | A | A | A |

TABLE 1-continued

| N | Structure | $^1$H-NMR | Molecule-Mass [g/mol] | HPLC/ MS (ESI) | human IC$_{50}$- Value [μM] | murine IC$_{50}$- Value [μM] | rate IC$_{50}$- Value [μM] |
|---|---|---|---|---|---|---|---|
| 57 | 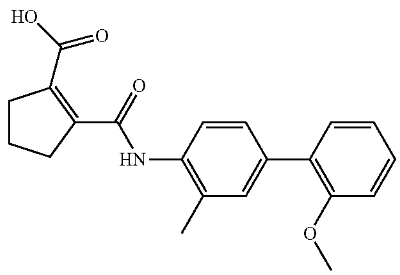 [SMILES: COc1ccccc1-c1ccc(NC(=O)C2=C(C(=O)O)CCC2)c(C)c1] | δ (CD3OD) = 1.97 (mC, 2H, CH2), 2.33 (s, 3H, CH3), 2.84 (mC, 2H, CH2), 2.94 (mC, 2H, CH2), 3.78 (s, 3H, O—CH3), 6.96-7.06 (m, 2H, CHAr), 7.25-7.35 (m, 4H, CHAr), 7.50 (mC, 1H, CHAr). | 351 | 352 [M + H]+ | A | B | B |
| 58 | 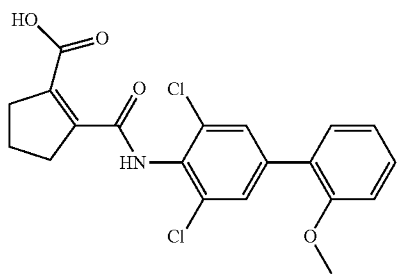 [SMILES: COc1ccccc1-c1cc(Cl)c(NC(=O)C2=C(C(=O)O)CCC2)c(Cl)c1] | δ (CD3OD) = 1.93 (mC, 2H, CH2), 2.87-2.95 (m, 4H, CH2), 3.83 (s, 3H, O—CH3), 7.01-7.10 (m, 2H, CHAr), 7.29-7.37 (m, 2H, CHAr), 7.56 (s, 2H, CHAr). | 405 | 406 [M + H]+ | A | B | B |
| 62 | 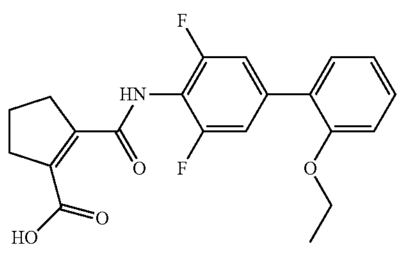 [SMILES: CCOc1ccccc1-c1cc(F)c(NC(=O)C2=C(C(=O)O)CCC2)c(F)c1] | δ (CD3OD) = 1.35 (mC, 3H, OCH2CH3), 2.00 (mC, 2H, CH2), 2.84 (mC, 2H, CH2), 2.94 (mC, 2H, CH2), 4.07 (mC, 2H, OCH2CH3), 6.98-7.08 (m, 2H, CHAr), 7.23 (mC, 2H, CHAr), 7.30-7.37 (m, 2H, CHAr). | 387 | 388 [M + H]+ | A | B | A |
| 63 | 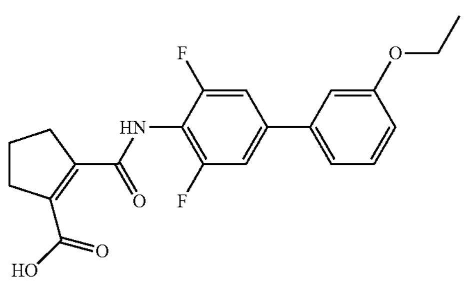 [SMILES: CCOc1cccc(-c2cc(F)c(NC(=O)C3=C(C(=O)O)CCC3)c(F)c2)c1] | δ (CD3OD) = 1.40 (mC, 3H, OCH2CH3), 1.99 (mC, 2H, CH2), 2.84 (mC, 2H, CH2), 2.93 (t, J = 7.5 Hz, 2H, CH2), 4.09 (mC, 2H, OCH2CH3), 6.94 (mC, 1H, CHAr), 7.13-7.20 (m, 2H, CHAr), 7.30-7.38 (m, 3H, CHAr). | 387 | 388 [M + H]+ | A | B | A |
| 64 | 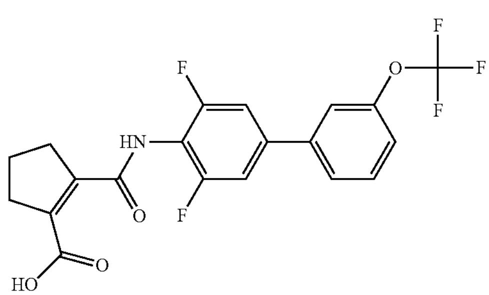 [SMILES: O=C(O)C1=C(C(=O)Nc2c(F)cc(-c3cccc(OC(F)(F)F)c3)cc2F)CCC1] | δ (CD3OD) = 1.99 (mC, 2H, CH2), 2.85 (mC, 2H, CH2), 2.91 (mC, 2H, CH2), 7.31-7.39 (m, 3H, CHAr), 7.54-7.59 (m, 2H, CHAr), 7.66 (mC, 2H, CHAr). | 427 | 428 [M + H]+ | A | C | N.D. |

TABLE 1-continued

| N | Structure | ¹H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 65 | 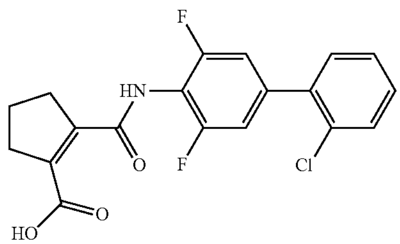 [SMILES: O=C(O)C1=C(C(=O)Nc2c(F)cc(-c3ccccc3Cl)cc2F)CCC1] | δ (CD3OD) = 2.00 (mC, 2H, CH2), 2.84 (mC, 2H, CH2), 2.94 (mC, 2H, CH2), 7.12 (s, 1H, CHAr), 7.14 (s, 1H, CHAr), 7.37-7.42 (m, 3H, CHAr), 7.49-7.53 (m, 1H, CHAr). | 377 | 378 [M + H]+ | A | A | N.D. |
| 66 | 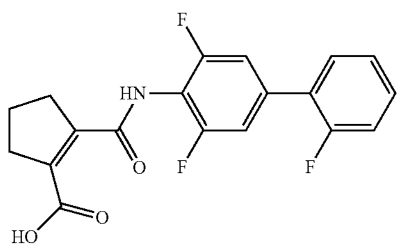 [SMILES: O=C(O)C1=C(C(=O)Nc2c(F)cc(-c3ccccc3F)cc2F)CCC1] | δ (CD3OD) = 2.00 (mC, 2H, CH2), 2.84 (mC, 2H, CH2), 2.94 (t, J = 7.8 Hz, 2H, CH2), 7.18-7.30 (m, 4H, CHAr), 7.38-7.46 (m, 1H, CHAr), 7.46-7.55 (m, 1H, CHAr). | 361 | 362 [M + H]+ | A | B | N.D. |
| 67 | 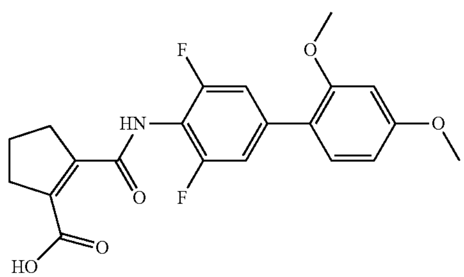 [SMILES: COc1ccc(-c2cc(F)c(NC(=O)C3=C(C(=O)O)CCC3)c(F)c2)c(OC)c1] | δ (CD3OD) = 1.94 (mC, 2H, CH2), 2.84-2.92 (m, 4H, CH2), 3.82 (s, 3H, O—CH3), 3.83 (s, 3H, O—CH3), 6.58-6.64 (m, 2H, CHAr), 7.14 (s, 1H, CHAr), 7.17 (s, 1H, CHAr), 7.26 (mC, 1H, CHAr). | 403 | 404 [M + H]+ | A | C | N.D. |
| 68 | 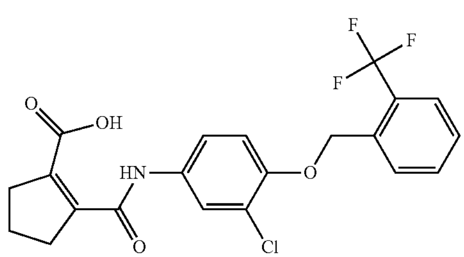 [SMILES: O=C(O)C1=C(C(=O)Nc2ccc(OCc3ccccc3C(F)(F)F)c(Cl)c2)CCC1] | δ = 1.90 (mC, 2H, CH2), 2.63 (mC, 2H, CH2), 2.74 (mC, 2H, CH2), 5.27 (s, 2H, O—CH2), 7.19-7.82 (m, 7H, CHAr), 10.23 (s, 1H, NH), 12.69 (s, 1H, OH). | 439 | 440 [M + H]+ | A | C | C |
| 69 | 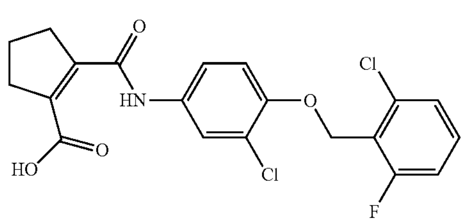 [SMILES: O=C(O)C1=C(C(=O)Nc2ccc(OCc3c(F)cccc3Cl)c(Cl)c2)CCC1] | δ = 1.89 (mC, 2H, CH2), 2.62 (mC, 2H, CH2), 2.74 (mC, 2H, CH2), 5.18 (mC, 2H, O—CH2), 7.27-7.77 (m, 6H, CHAr), 10.21 (s, 1H, NH), 12.69 (s, 1H, OH). | 423 | 424 [M + H]+ | A | A | N.D. |
| 72 | 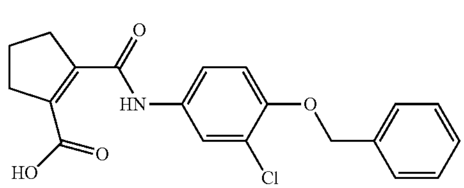 [SMILES: O=C(O)C1=C(C(=O)Nc2ccc(OCc3ccccc3)c(Cl)c2)CCC1] | δ = 1.73 (mC, 2H, CH2), 2.46 (mC, 2H, CH2), 2.57 (mC, 2H, CH2), 4.99 (mC, 2H, O—CH2), 7.00-7.62 (m, 8H, CHAr), 10.02 (s, 1H, NH), 12.70 (s, 1H, OH). | 371 | 372 [M + H]+ | A | B | N.D. |

TABLE 1-continued

| N | Structure | ¹H-NMR | Molecule-Mass [g/mol] | HPLC/MS (ESI) | human IC$_{50}$-Value [μM] | murine IC$_{50}$-Value [μM] | rate IC$_{50}$-Value [μM] |
|---|---|---|---|---|---|---|---|
| 74 | [structure] | δ = 1.82 (mC, 2H, CH2), 2.55 (mC, 2H, CH2), 2.67 (mC, 2H, CH2), 5.11 (mC, 2H, O—CH2), 7.14-7.72 (m, 7H, CHAr), 10.18 (s, 1H, NH), 12.53 (s, 1H, OH). | 389 | 390 [M + H]+ | A | A | N.D. |
| 76 | [structure] | δ (CDCl3) = 2.01 (mC, 2H, CH2), 2.99-3.04 (m, 4H, CH2), 3.81 (s, 3H, O—CH3), 6.96-7.04 (m, 2H, CHAr), 7.27-7.41 (m, 4H, CHAr), 8.19 (s, 1H, NH), 8.28 (mC, 1H, CHAr). | 355 | 356 [M + H]+ | A | B | A | abbreviations: N.D. = not determined, m$_c$= multiplet center
inhibition activity is defined: A: 0-800 nM B: 800-1500 nM C: >1500 nM The compounds of formula (I) may be obtained via various methods, including the method described in JP-A-50-121428. In preferred embodiments of the methods of the invention the two following methods of synthesis are used.

Method 1: In a first step the cycloalkene-1,2-dicarboxic acids can be obtained from the corresponding α,α'-dibromo alkanedicarboxylic acids as described by R. N. Mc Donald and R. R. Reitz, J. Org. Chem. 37, (1972) 2418-2422. Cyclopentene-1,2-dicarboxylic acid can also be obtained in large amounts from pimelic acid [D. C. Owsley and J. J. Bloomfield, Org. Prep. Proc. Int. 3, (1971) 61-70; R. Willstätter, J. Chem. Soc. (1926), 655-663].

Dicarboxylic acids substituted in or on the ring system can be synthesized in general via the cyanhydrine synthesis [Shwu-Jiüan Lee et.al., Bull. Inst. Chem. Academia Sinica Number 40, (1993), 1-10 or B. R. Baker at al., J. Org. Chem. 13, 1948, 123-133; and B. R. Baker at al., J. Org. Chem. 12, 1947, 328-332; L. A. Paquette et. al., J. Am. Chem. Soc. 97, (1975), 6124-6134].

The dicarboxylic acids can then be converted into the corresponding acid anhydrides by reacting them with acetic acid anhydride [P. Singh and S. M. Weinreb, Tetrahedron 32, (1976), 2379-2380].

Other methods for preparing different acid anhydrides of formula (II) are described in V. A. Montero at al., J. Org. Chem. 54, (1989), 3664-3667; P. ten Haken, J. Heterocycl. Chem. 7, (1970), 1211-1213; K. Alder, H. Holzrichter, J. Lieb. Annalen d. Chem. 524, (1936), 145-180; K. Alder, E. Windemuth, J. Lieb. Annalen d. Chem. 543, (1940), 56-78; and W. Flaig, J. Lieb. Annalen d. Chem. 568, (1950), 1-33.

These anhydrides may then be reacted with the corresponding amines to the desired amides of formula (I). This reaction can be carried out either by use of the reaction conditions as described in J. V. de Julian Ortiz et al., J. Med. Chem. 42, (1999), 3308 (designated route A in Example 1) or by use of 4-dimethylamino pyridine (designated route B in Example 1).

Method 2: The amides of formula (I) can also be synthesized by reacting an amine of the formula (IV) with an arylboronic-acid of the general formula (V) [M. P. Winters, Tetrahedron Lett, 39, (1998), 29332936].

Biarylaniline can be synthesized in general via the palladium coupling [G. W. Kabalka et al., Chem. Commun., (2001), 775; A. Demeter, Tetrahedron Lett. 38; (1997), 5219-5222; V. Snieckus, Chem. Commun. 22, (1999), 2259-2260].

Method 3: The amides of formula (I) can also be synthesized by reacting an halogen derivative of the formula (VI) with an arylboronic acid of the general formula (VII) [N. E. Leadbeater, S. M. Resouly, Tetrahedron, 55, 1999, 11889-11894].

The calcium salts of the present invention can be used for a variety of human and animal diseases, preferably human diseases, where inhibition of the pyrimidine metabolism is beneficial. Such diseases are:

fibrosis, uveitis, rhinitis, asthma or athropathy, in particular, arthrosis all forms of rheumatism acute immunological events and disorders such as sepsis, septic shock, endotoxic shock, Gram-negative sepsis, toxic shock syndrome, acute respiratory distress syndrome, stroke, reperfusion injury, CNS injury, serious forms of allergy, graft versus host and host versus graft reactions, alzheimer's or pyresis, restenosis, chronic pulmonary inflammatory disease, silicosis, pulmonary sarcosis, bone resorption disease. These immunological events also include a desired modulation and suppression of the immune system;

all types of autoimmune diseases, in particular rheumatoid arthritis, rheumatoid spondylitis, osteoarthritis, gouty arthritis, multiple sclerosis, insulin dependent diabetes mellitus and non-insulin dependent diabetes, and lupus erythematosus, ulcerative colitis, Morbus Crohn, inflammatory bowel disease, as well as other chronic inflammations, chronic diarrhea;

dermatological disorders such as psoriasis
progressive retinal atrophy
all kinds of infections including opportunistic infections.

The calcium salts according to the invention and medicaments prepared therewith are generally useful for the treatment of cell proliferation disorders, for the treatment or prophylaxis, immunological diseases and conditions (as for instance inflammatory diseases, neuroimmunological diseases, autoimmune diseases or other).

The calcium salts of the present invention are also useful for the development of immunomodulatory and anti-inflammatory medicaments or, more generally, for the treatment of diseases where the inhibition of the pyrimidine biosynthesis is beneficial.

The calcium salts of the present invention are also useful for the treatment of diseases which are caused by malignant cell proliferation, such as all forms of hematological and solid cancer. Therefore the compounds according to the invention and medicaments prepared therewith are generally useful for regulating cell activation, cell proliferation, cell survival, cell differentiation, cell cycle, cell maturation and cell death or to induce systemic changes in metabolism such as changes in sugar, lipid or protein metabolism. They can also be used to support cell generation poiesis, including blood cell growth and generation (prohematopoietic effect) after depletion or destruction of cells, as caused by, for example, toxic agents, radiation, immunotherapy, growth defects, malnutrition, malabsorption, immune dysregulation, anemia and the like or to provide a therapeutic control of tissue generation and degradation, and therapeutic modification of cell and tissue maintenance and blood cell homeostasis.

These diseases and conditions include but are not limited to cancer as hematological (e.g. leukemia, lymphoma, myeloma) or solid tumors (for example breast, prostate, liver, bladder, lung, esophageal, stomach, colorectal, genitourinary, gastrointestinal, skin, pancreatic, brain, uterine, colon, head and neck, and ovarian, melanoma, astrocytoma, small cell lung cancer, glioma, basal and squamous cell carcinoma, sarcomas as Kaposi's sarcoma and osteosarcoma), treatment of disorders involving T-cells such as aplastic anemia and DiGeorge syndrome, Graves' disease.

Leflunomide, was previously found to inhibit HCMV replication in cell culture. Ocular herpes is the most common cause of infectious blindness in the developed world. There are about 50.000 cases per year in the US alone, of which 90% are recurrences of initial infections. Recurrences are treated with antivirals and corticosteroids. Cytomegalovirus another herpes virus is a common cause of retinal damage and blindness in patients with aids. The compounds of the present invention can be used alone or in combination with other antiviral compounds such as Ganciclovir and Foscarnet to treat such diseases.

The calcium salts of the present invention can further be used for diseases that are caused by protozoal infestations in humans and animals. Such veterinary and human pathogenic protozoas are preferably intracellular active parasites of the phylum Apicomplexa or Sarcomastigophora, especially *Trypanosoma, Plasmodia, Leishmania, Babesia* and *Theileria, Cryptosporidia, Sacrocystida, Amoebia, Coccidia* and *Trichomonadia*. These active substances or corresponding drugs are especially suitable for the treatment of Malaria tropica, caused by *Plasmodium falciparum*, Malaria tertiana, caused by *Plasmodium vivax* or *Plasmodium ovale* and for the treatment of Malaria quartana, caused by *Plasmodium malariae*. They are also suitable for the treatment of Toxoplasmosis, caused by *Toxoplasma gondii*, Coccidiosis, caused for instance by *Isospora belli*, intestinal Sarcosporidiosis, caused by *Sarcocystis suihominis*, dysentery caused by *Entamoeba histolytica*, Cryptosporidiosis, caused by *Cryptosporidium parvum*, Chargas' disease, caused by *Trypanosoma cruzi*, sleeping sickness, caused by *Trypanosoma brucei rhodesiense* or *gambiense*, the cutaneous and visceral as well as other forms of Leishmaniosis. They are also suitable for the treatment of animals infected by veterinary pathogenic protozoa, like *Theileria parva*, the pathogen causing bovine East coast fever, *Trypanosoma congolense congolense* or *Trypanosoma vivax vivax, Trypanosoma brucei brucei*, pathogens causing Nagana cattle disease in Africa, *Trypanosoma brucei evansi* causing Surra *Babesia bigemina*, the pathogen causing Texas fever in cattle and buffaloes, *Babesia Bovis*, the pathogen causing european bovine Babesiosis as well as Babesiosis in dogs, cats and sheep, *Sarcocystis ovicanis* and *ovifelis* pathogens causing Sarcocystiosis in sheep, cattle and pigs, Cryptosporidia, pathogens causing Cryptosporidioses in cattle and birds, *Eimeria* and *Isospora* species, pathogens causing Coccidiosis in rabbits, cattle, sheep, goats, pigs and birds, especially in chickens and turkeys. The use of the compounds of the present invention is preferred in particular for the treatment of Coccidiosis or Malaria infections, or for the preparation of a drug or feed stuff for the treatment of these diseases. This treatment can be prophylactic or curative. In the treatment of malaria, the compounds of the present invention may be combined with other anti-malaria agents.

The calcium salts of the present invention can further be used for viral infections or other infections caused for instance by *Pneumocystis carinii*.

Preferably, the diseases or medical conditions to be treated or prevented by the calcium salts according to the present invention are selected from the group comprising graft versus host and host versus graft reactions, rheumatoid arthritis, multiple sclerosis, lupus erythematosus, inflammatory bowel disease, and psoriasis.

The calcium salts of the compounds of the formula (I) can be administered to animals, preferably to mammals, and in particular to humans, dogs and chickens as therapeutics per se, as mixtures with one another or in the form of pharmaceutical preparations which allow enteral or parenteral use and which as active constituent contain an effective dose of at least one of the aforementioned calcium salts of a compound of the formula (I), in addition to customary pharmaceutically innocuous excipients and additives.

The therapeutics can be administered orally, e.g. in the form of pills, tablets, coated tablets, sugar coated tablets, hard and soft gelatin capsules, solutions, syrups, emulsions or suspensions or as aerosol mixtures. Administration, however, can also be carried out rectally, e.g. in the form of suppositories, or parenterally, e.g. in the form of injections or infusions, or percutaneously, e.g. in the form of ointments, creams or tinctures.

In addition to the aforementioned salts of the active compounds of formula (I), the pharmaceutical composition can contain further customary, usually inert carrier materials or excipients. Thus, the pharmaceutical preparations can also contain additives, such as, for example, fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for changing the osmotic pressure, coating agents or antioxidants. They can also contain the aforementioned salts of two or more compounds of the formula (I) and also other therapeutically active substances.

Thus, the salts of the present invention can be used alone or in combination with other active compounds—for example with medicaments already known for the treatment of the aforementioned diseases, whereby in the latter case a favorable additive, amplifying effect is noticed. Suitable amounts to be administered to humans range from 5 to 500 mg.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 to 100 mg/kg animal body weight preferably 1 to 50 mg/kg. Suitable dosage rates for larger mammals, for example humans, are of the order of from about 10 mg to 3 g/day, conveniently administered once, in divided doses 2 to 4 times a day, or in sustained release form.

In general, a daily dose of approximately 10 mg to 5000 mg, preferably 50 to 500 mg, per human individual is appropriate in the case of the oral administration which is the preferred form of administration according to the invention. In the case of other administration forms too, the daily dose is in similar ranges.

BRIEF DESCRIPTION OF THE FIGURES

FIG. 6: PXRD of vidofludimus free acid.

EXAMPLES

Figure 1:
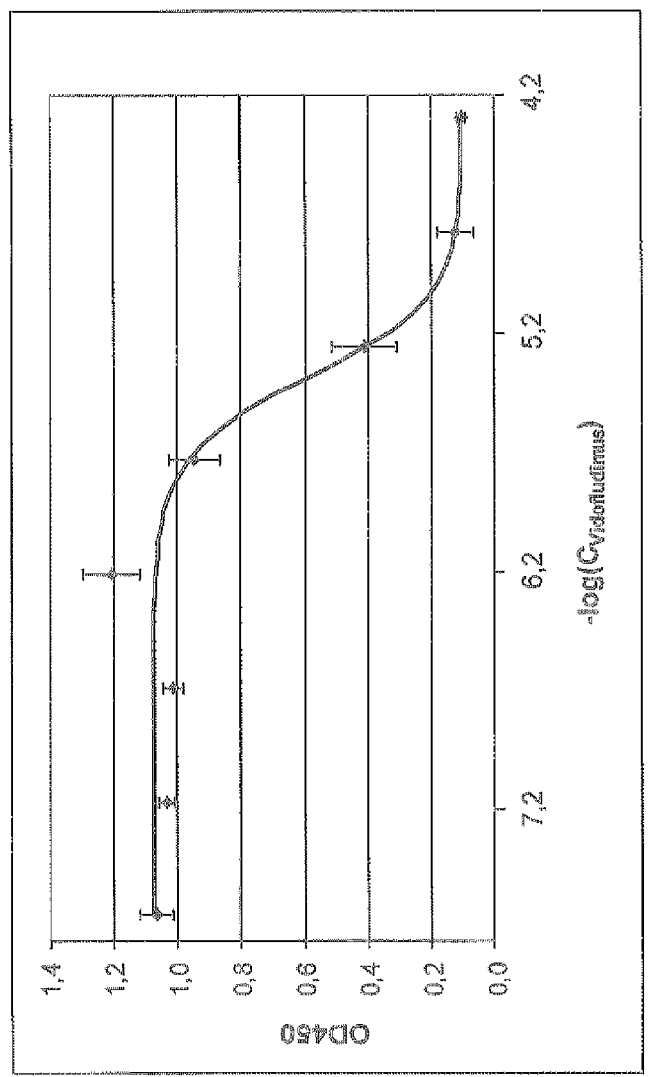
FIG. 1: Reduction of human T-cell proliferation caused by 2-(Biphenyl-4-ylcarbamoyl)-cyclopent-1-enecarboxylic acid used in a concentration of 100 µM.

The invention is further illustrated by the following non-limiting Examples. The data shown for the specific compounds depicted in above Table 1 also relates to specific Examples of the present invention.

Experimental/Instrument Settings $^1$H-NMR: $^1$H-NMR spectra were recorded using a Bruker DPX300 spectrometer with a proton frequency of 300.13 MHz, a 30° excitation pulse, and a recycle delay of 1 s. 16 scans were accumulated, D2O; MeOD or d6-DMSO was used as the solvent.

DSC: Differential scanning calorimetry was carried out with a Perkin Elmer DSC-7 instrument (closed gold sample pan under $N_2$ atmosphere). The sample are heated up to the melting point at a rate of 10K/min), then cooled down (cooling rate 200K/min) and afterwards heated up again at a rate of 10K/min.

DVS (SMS): Surface Measurement Systems Ltd. DVS-1 water vapour sorption analyzer. The sample is placed on a platinum sample pan and allowed to equilibrate at a given relative humidity (r.h.), usually 50% r.h. Then, a pre-defined humidity program was started with a scanning rate of 5% r.h. change per hour. First step: from 50% r.h. to 0% r.h, (in case of a possibly hydrate as starting material 50 to 95% r.h.), second step: from 0% to 95% r.h. (in case of a possibly hydrate as starting material 95 to 0% r.h.)

FT-Raman spectroscopy: FT-Raman spectra were recorded on a Bruker RFS100 FT-Raman system with a near infrared Nd:YAG laser operating at 1064 nm and a liquid nitrogen-cooled germanium detector. For each sample, a minimum of 64 scans with a resolution of 2 $cm^{-1}$ were accumulated. 300 mW nominal laser power was used. The FT-Raman data are shown in the region between 3500 to 100 $cm^{-1}$. Below 100 $cm^{-1}$ the data are unreliable due to the Rayleigh filter cut-off.

Optical Microscopy: Leitz Orthoplan 110680 microscope equipped with a Leica DFC280 camera and IM50 v.5 image-capturing software. Images were recorded with or without crossed polarizers and with 4×, 10×, or 25× magnification.

Powder X-ray diffraction: Bruker D8; Copper $K_\alpha$ radiation, 40 kV/40 mA; LynxEye detector, 0.02° 2Θ step size, 37 s step time. Sample preparation: The samples were generally measured without any special treatment other than the application of slight pressure to get a flat surface. Silicon single crystal sample holders were used (0.1, 0.5 or 1 mm deep). The samples were rotated during the measurement.

Raman microscopy: Renishaw in Via Reflex Raman System. Stabilized diode laser with 785 nm excitation and an NIR enhanced Peltier-cooled CCD camera as the detector. Measurements were carried out with a long working distance 20× objective. Wavenumber range 2000-100 $cm^{-1}$, 10 s detection time, three accumulations per spectrum.

Solvents: For all experiments, Fluka, Merck or ABCR analytical grade solvents were used.

TG-FTIR: Thermogravimetric measurements were carried out with a Netzsch Thermo-Microbalance TG 209 coupled to a Bruker FTIR Spectrometer Vector 22 or IFS 28 (sample pans with a pinhole, N2 atmosphere, heating rate 10° C./min, range 25° C. to 350° C.).

HPLC: HPLC was performed with a Dionex UltiMate 3000 liquid chromatograph comprising a solvent Rack, a vacuum degasser, a binary pump (mikro), a static mixer (500 µl), an autosampler, a 25 µl sample loop, a 100 µl syringe, a column oven and a DAD detector (semimicro measuring cell), which was set up for UV analysis. Data analysis was done with Chromeleon® 6.80 SP3. Compounds were separated at 30° C. on a Phenomenex Onyx™ Monolithic C18 50×2 mm column. The injection volume was 2 µl and the detection wavelength was 305 nm. As mobile phase, a gradient of 0.1% formic acid in HPLC grade water/acetonitrile was used, starting at a concentration of 5% acetonitrile. The starting concentration was held for 1 minute, then the gradient was ramped linearly to 95% acetonitrile over the course of 2 min, held for 0.7 min at 95% acetonitrile, after which it was returned to 5% acetonitrile within 0.1 min and kept constant for 0.7 min to re-equilibrate the column. The mobile phase flow rate was 1.5 nil/min.

Example 1

Synthesis of Compounds of Formula (I)

The synthesis of compounds of formula (I) is described in detail in WO 2003/0006425, which is incorporated herein by reference.

Example 2

Inhibition Assay of DHODH Activity

The standard assay mixture contained 50 µM decyclo ubichinone, 100 µM dihydroorotate, 60 µM 2,6-dichloroindophenol, as well as 20 mU DHODH. The volume activity of the recombinant enzyme used was 30 U/ml. Measurements were conducted in 50 mM TrisHCl (150 mM KCl, 0.1% Triton X-100, pH 8.0) at 30° C. in a final volume of 1 ml. The components were mixed, and the reaction was started by adding dihydroorotate. The course of reaction was followed by spectrophotometrically measuring the decrease in absorption at 600 nm for 2 min.

Inhibitory studies were conducted in a standard assay with additional variable amounts of inhibitor. For the determination of the $IC_{50}$ values (concentration of inhibitor required for 50% inhibition) at least five different inhibitor concentrations were applied.

These investigations were carried out with recombinant human as well as with recombinant murine DHODH provided by Prof. M. Löffler, Marburg, Germany [M. Löffler, Chem. Biol. Interact. 124, (2000), 61-76].

As a reference the active metabolite of leflunomide A77-1726 (Compound 12) was used [J. Jöckel et. al. Biochemical Pharmacology 56 (1998), 1053-1060].

The results of the inhibition assay are shown in the above Table 1. It is evident from the comparison of the $IC_{50}$-values that the compounds used for the preparation of the salts according to the present invention not only have a comparable or even better inhibitory activity on the human enzyme than the active metabolite of leflunomide but also a higher specificity for the human enzyme.

Example 3

Proliferation Assay of Human T-cells

Human peripheral blood mononuclear cells (PBMC) were obtained from healthy volunteers and transferred to RPMI1640 cell culture medium containing 10% dialyzed fetal calf serum. 80.000 cells per well were pipetted into a 96-well plate and phytohemagglutinin (PHA) was added in phosphate buffered saline to a final concentration of 20 µg/ml to stimulate T-cell proliferation. Vidofludimus was added in dimethyl sulfoxide (DMSO, final concentration: 0.1 Vol %) to final concentrations ranging from 20 nM to 50 µM. After incubation for 48 hours, cell proliferation was quantified using the "cell proliferation ELISA BrdU" (Roche) according to the manufacturer's instructions. Half maximal inhibition ($IC_{50}$) was calculated using a 4-parameter sigmoidal curve fit. T-cell proliferation was inhibited by Vidofludimus with an $IC_{50}$ of 4.1 µM. (see FIG. 1).

Example 4

Preparation of the Calcium Salts 300.4 mg of Vidofludimus free acid was dissolved in 18 mL of DCM/MeOH (3:1) and sonicated for 8 minutes. 31.5 mg of calcium hydroxide was suspended in 3 mL of DCM/MeOH (3:1); this was slowly added to the Vidofludimus free acid solution. The slight suspension was stirred overnight at 25° C. The solvent was partially evaporated under nitrogen flow at 25° C. A thick light yellow suspension was observed. The solid was recovered by filtration and washed with DCM/MeOH (3:1). The material was dried for 15 min under vacuum at 25° C. The material was shown to be crystalline using the methods described in the following.

From elemental analysis, the ratio of fluorine to calcium was calculated. The elemental composition is essentially consistent with a hemi-calcium-salt.

Figure 3:
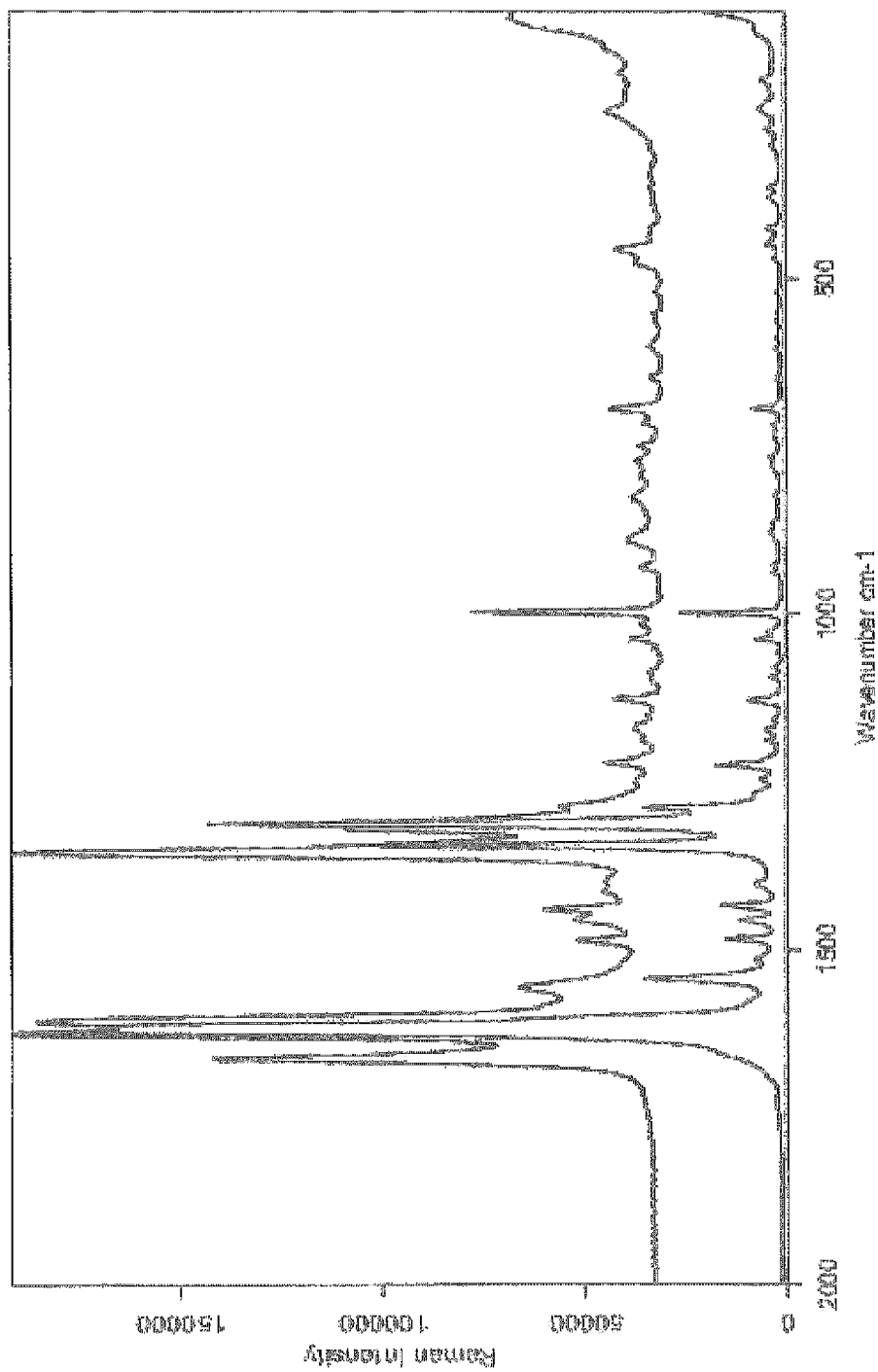
FIG. 3: Raman spectrum for Ca salt (top trace) and free acid (bottom)

The Raman spectrum of the newly formed compound demonstrated differences to that of the free acid (see FIG. 3 for both spectra.). Note that a Raman spectrum that is not simply the superposition of the free acid, the salt former and the solvent spectra, e.g., a Raman spectrum where new peaks or shifted peaks are observed, may correspond to a salt. However, from the Raman spectrum alone, it cannot be determined whether crystalline salt formation has occurred. Peak shifts could also be due, in principle, to complexation of the free acid and salt former as an amorphous product, to polymorphs of either the free acid or salt former, to impurities, or to degradation products. Therefore, the integrity of the molecular structure was confirmed by $^1$H-NMR.

Figure 4:
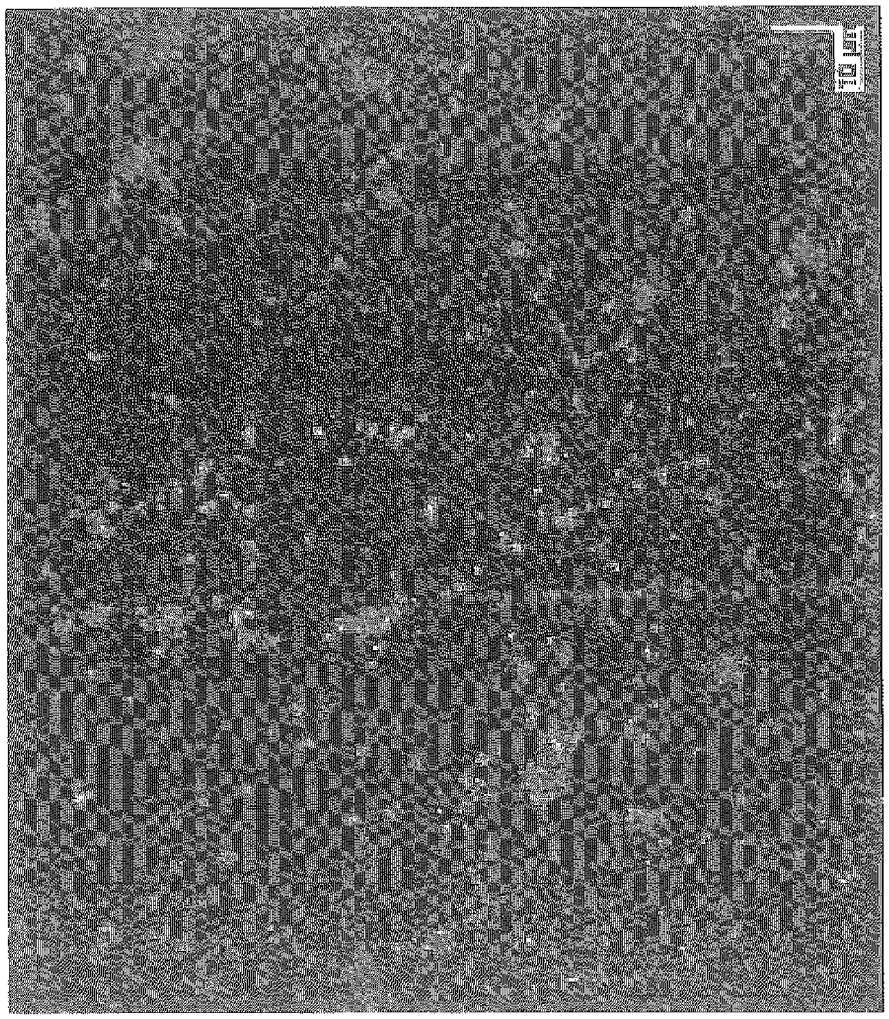
FIG. 4: Optical microscopy with cross polarizers of the vidofludimus Ca salt.
Figure 5:
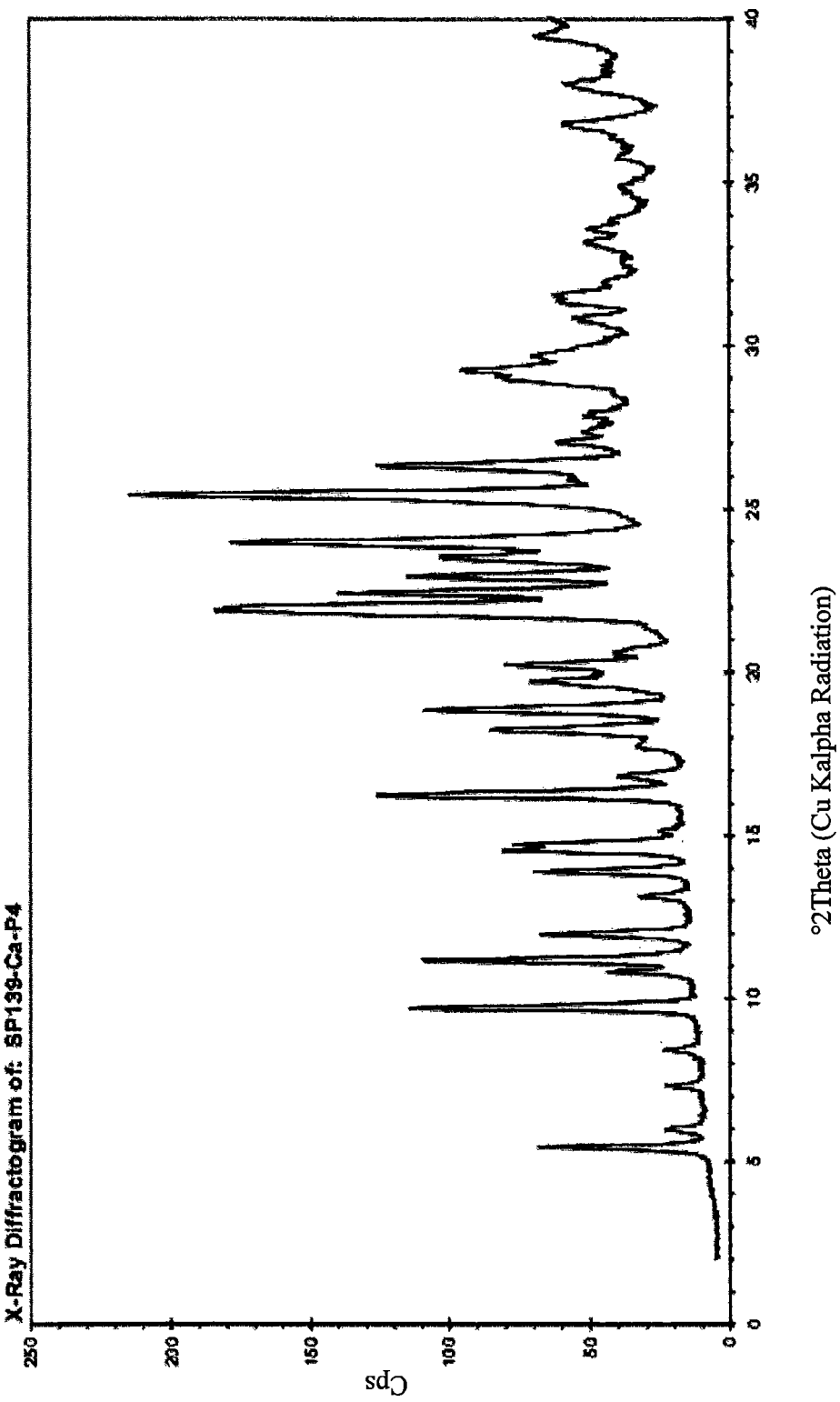
FIG. 5: PXRD of the vidofludimus Ca salt.

In addition, the powder X-ray diffraction shown in FIG. 5 show that crystalline material was obtained, however with a pattern different from that of the free acid (see FIG. 6). With light microscopy the crystals were visualized (FIG. 4), DSC (differential scanning calorimetry) demonstrated a melting point of about 155° C. (indicating a melting of a solvate and of a non-solvated form), TG-FTIR (thermogravimetric analyzer-coupled Fourier-Transform. Infrared) indicates that probably a methanol solvate and a hydrate were formed and dynamic vapor sorption revealed desolvation followed by 0.3% water uptake at about 85% r.h. and 0.4% water uptake at 95% r.h. (not reversible).

Example 5

Investigation of the Solubility of the Compounds

Aqueous solubilities of Vidofludimus free acid (2-(3-Fluoro-3'-methoxybiphenyl-4-ylcarbamoyl)-cyclopent-1-enecarboxylic acid), its potassium salt and its Calcium salt were examined. The principle of the method was based on the OECD Guideline for the testing of chemicals, 105 "Water Solubility". 2 mg of the experimental compounds were weighed into Eppendorf vials of 1.5 ml. Subsequently, water was added to arrive at a concentration of 5 mg/ml. After preparation of the solubility samples they were incubated for 24 h at 23° C. under continuous shaking. Then the samples were centrifuged to separate the precipitate from the dissolved compound. The supernatants were transferred into labelled HPLC vials for quantification by HPLC-UV. Finally, these HPLC samples were analysed on the HPLC-UV System and their contents were calculated from the calibration curves, The concentration of compound in the supernatant equals its solubility in water. The following aqueous solubilities were found for Vidofludimus free acid and its potassium- and calcium salt:

TABLE 2 solubility of vidofludimus calcium salt in comparison with potassium salt and free acid

|  | Vidofludimus | | |
| --- | --- | --- | --- |
|  | free acid | Potassium salt | Calcium salt |
| Solubility [μg/ml] | 9.5 | 4700 | 16.2 |

Example 6

Determination of the Bioavailability

Oral bioavailabilities of the Calcium salt and the free acid of Vidofludimus were compared in male Wistar rats. The free acid or the Calcium salt was filled into gelatine capsules and the animals received a single administration at a dose level of approximately 10 mg free acid equivalents per kilogram body weight.

Four male Wistar rats (body weight range: 250-275 g) per group were treated with either Vidofludimus free acid or its Calcium salt. The capsules were administered into the oesophagus of the animals using an application device. Venous blood samples were taken from the animals under isoflurane anaesthesia at the following time points after administration: 30 min; 1 h; 2 h; 4 h; 6 h; 8 h; 24 h; 28 h; 32 h and 48 h. Coagulation was inhibited using Na-heparin and plasma was generated by centrifugation of the blood samples. Plasma samples were analyzed for Vidofludimus by LC-MS/MS and pharmacokinetic parameters were calculated according to the mixed log linear trapezoidal method.

To examine the potassium salt, six female Lewis rats (body weight ca. 200 g) are treated with either Vidofludimus free acid or its potassium salt at a dose level of 30 mg/kg (free acid equivalents). The compounds are formulated in 0.5% methylcellulose in phosphate buffered saline and the animals are treated by oral gavage. Venous blood samples are taken from the animals under isoflurane anaesthesia at the following time points after administration: 30 min; 1 h; 2 h; 4 h; 8 h; 26 h; 33 h; 48 h and 72 h. Coagulation is inhibited using Na-heparin and plasma is generated by centrifugation of the blood samples. Plasma samples are analyzed for Vidofludimus by LC-MS/MS and pharmacokinetic parameters (AUC) are calculated according to the linear trapezoidal rule method.

Figure 2:
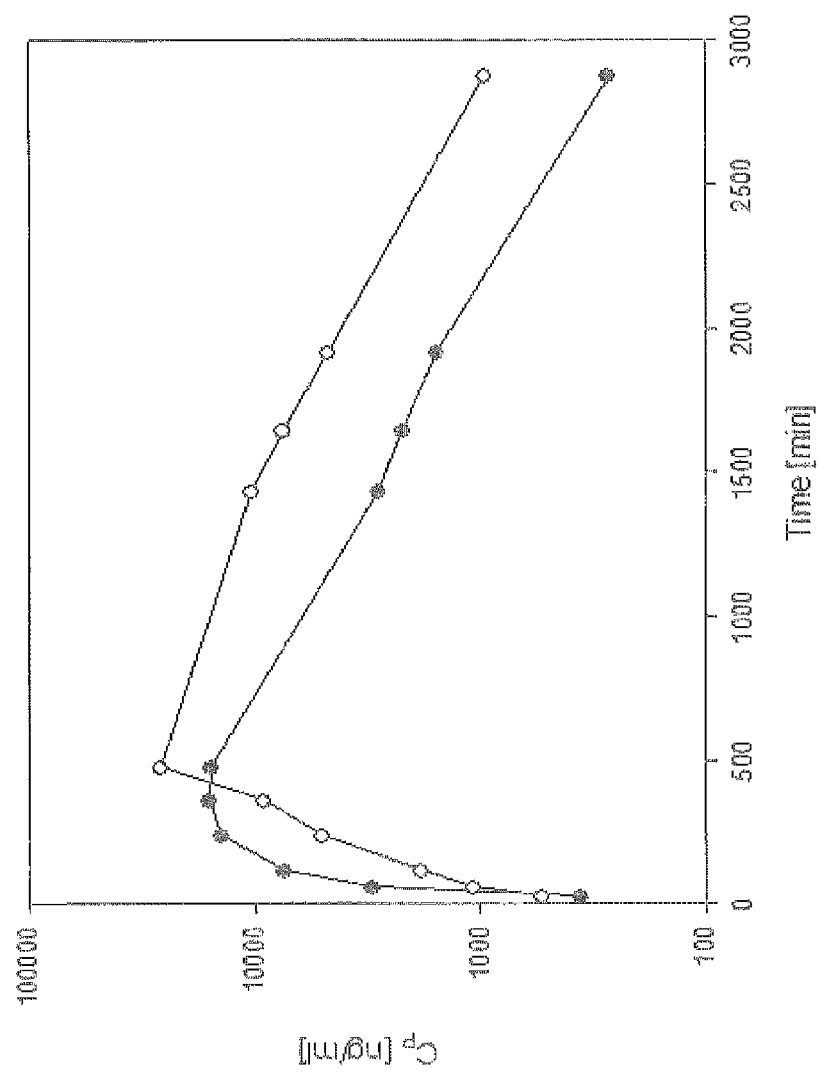
FIG. 2: Comparison of plasma levels of vidofludimus free acid (filled dots) and its calcium salt (unfilled dots) in rats after a single oral dosage of 10 mg/kg body weight.

Oral bioavailabilities of the salts are evaluated by comparing the areas under the plasma-concentration-time-curves (AUCs) and the maximally attained plasma concentrations (Cmax values) of Vidofludimus after administration of the salt with those observed after administration of the free acid. These ratios are shown in Table 3 and FIG. 2.

TABLE 3

Comparison of PK parameters after oral application of Vidofludimus to rats

| Compound | $AUC_{inf}/AUC_{inf,free\ acid}$ | $C_{max}/C_{max,free\ acid}$ |
| --- | --- | --- |
| Vidofludimus free acid | 1 | 1 |
| Potassium salt | 0.96 | 1.09 |
| Calcium salt | 1.72 | 1.67 |

Example 7

Determination of the Long-Term Stability

The compounds were stored for 18 months at ambient conditions (20-25° C., 30-60% relative humidity) and subsequently analysed by HPLC for purity.

| Compound | Occurrence of hydrolysis product in HPLC after 18 months storage | Peak area |
| --- | --- | --- |
| Vidofludimus free acid | Below LOD* | >99% |
| Ca salt | Below LOD* | >99% |

*LOD for hydrolysis product: 0.1 μg/ml

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding U.S. Provisional Application Ser. No. 61/360,670, filed Jul. 1, 2010, are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. The calcium salt of a compound of the general formula (I)

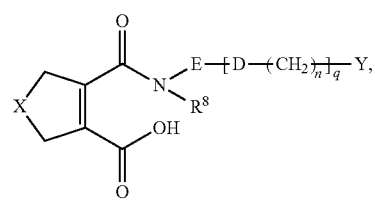

wherein
X is $CH_2$, S, or O;
D is O or S;
$R^8$ is hydrogen or alkyl;
E is an optionally substituted phenylene group;
Y is a monocyclic or bicyclic substituted or unsubstituted 6-9 membered ring system which optionally contains one or more heteroatoms selected from N or S and which contains at least one aromatic ring;
n is 0 or 1; and
q is 0 or 1;
with the proviso that the calcium salts of compounds wherein X=$CH_2$, q=0, Y=unsubstituted phenyl and E=unsubstituted phenylene are excluded,
or a hydrate thereof.

2. The calcium salt or hydrate thereof according to claim 1, wherein $R^8$ is hydrogen or methyl.

3. The calcium salt or hydrate thereof according to claim 1, wherein Y is substituted or unsubstituted phenyl.

4. The calcium salt or hydrate thereof according to claim 1, wherein q is 0.

5. The calcium salt or hydrate thereof according claim 1, wherein E is an unsubstituted phenylene group or a phenylene group which is substituted with one or more groups independently selected from halogen, nitro or alkoxy.

6. The calcium salt or hydrate thereof according to claim 1, wherein Y is an unsubstituted phenyl group or a phenyl group which is substituted with one or more groups independently selected from halogen, alkyl, alkoxy, haloalkoxy, haloalkyl or CN.

7. The calcium salt or hydrate thereof according to claim 1, wherein Y is a phenyl group which is substituted with one or more groups independently selected from methoxy or trifluoromethoxy.

8. The calcium salt or hydrate thereof according to claim 1, wherein the compound of formula 1 is 2-(3-fluoro-3'-methoxy-biphenyl-4-ylcarbamoyl)-cyclopent-1-enecarboxylic acid.

9. A pharmaceutical composition comprising a salt or hydrate thereof as defined in claim 1, together with a pharmaceutically acceptable diluent or carrier.

10. The calcium salt or hydrate thereof according to claim 7, wherein Y is a phenyl group which is substituted with one or more methoxy groups.

11. The calcium salt or hydrate thereof according to claim 1, wherein n is 0.

12. The calcium salt or hydrate thereof according to claim 1, wherein E is a phenylene group which is substituted with one fluorine or chlorine atom, one methoxy group or with four fluorine atoms.

13. The calcium salt or hydrate thereof according to claim 1, wherein E is a phenylene group which is substituted with one or four fluorine atoms.

14. The calcium salt or hydrate thereof according to claim 1, wherein the compound of formula (I) is:
- 2-((4-(benzyloxy)phenyl)carbamoyl)cyclopent-1-enecarboxylic acid,
- 2-((2'-fluoro-[1,1'-biphenyl]-4-yl)carbamoyl)cyclopent-1-enecarboxylic acid,
- 2-((2'-chloro-[1,1'-biphenyl]-4-yl)carbamoyl)cyclopent-1-enecarboxylic acid,
- 2-((2'-methoxy-[1,1'-biphenyl]-4-yl)carbamoyl)cyclopent-1-enecarboxylic acid,
- 2-((4-((2,6-difluorobenzyl)oxy)phenyl)carbamoyl)cyclopent-1-enecarboxylic acid,
- 2-((2'-ethoxy-3-fluoro-[1,1'-biphenyl]-4-yl)carbamoyl)cyclopent-1-enecarboxylic acid,
- 2-((2-chloro-3'-cyano-[1,1'-biphenyl]-4-yl)carbamoyl)cyclopent-1-enecarboxylic acid,
- 2-((2-chloro-4'-methoxy-[1,1'-biphenyl]-4-yl)carbamoyl)cyclopent-1-enecarboxylic acid,
- 2-((3-chloro-4-(6-methoxypyridin-3-yl)phenyl)carbamoyl)cyclopent-1-enecarboxylic acid,
- 2-((4'-methoxy-2-methyl-[1,1'-biphenyl]-4-yl)carbamoyl)cyclopent-1-enecarboxylic acid,
- 2-((3,5-dibromo-4-((2,5difluorobenzyl)oxy)phenyl)carbamoyl)cyclopent-1-enecarboxylic acid,
- 2-((3,5-dibromo-4-((3,4-difluorobenzyl)oxy)phenyl)carbamoyl)cyclopent-1-enecarboxylic acid,
- 2-((3-fluoro-3'-methoxy-[1,1'-biphenyl]-4-yl)carbamoyl)cyclopent-1-enecarboxylic acid,
- 2-((3,3'-difluoro-[1,1'-biphenyl]-4-yl)carbamoyl)cyclopent-1-enecarboxylic acid,
- 4-((4-(benzyloxy)-3,5-dibromophenyl)carbamoyl)-2,5-dihydrothiophene-3-carboxylic acid,
- 2-((3,4',5-trifluoro-3'-methyl-[1,1'-biphenyl]-4-yl)carbamoyl)cyclopent-1-enecarboxylic acid,
- 2-((3,5'-difluoro-2'-methoxy-[1,1'-biphenyl]-4-yl)carbamoyl)cyclopent-1-enecarboxylic acid,
- 2-((2'-methoxy-3-nitro-[1,1'-biphenyl]-4-yl)carbamoyl)cyclopent-1-enecarboxylic acid,
- 2-((3-methoxy-[1,1'-biphenyl]-4-yl)carbamoyl)cyclopent-1-enecarboxylic acid,
- 2-((2'-chloro-3-methoxy-[1,1'-biphenyl]-4-yl)carbamoyl)cyclopent-1-enecarboxylic acid,
- 2-((3-methoxy-3'-(trifluoromethoxy)-[1,1'-biphenyl]-4-yl)carbamoyl)cyclopent-1-enecarboxylic acid,
- 2-((2'-fluoro-3-methoxy-[1,1'-biphenyl]-4-yl)carbamoyl)cyclopent-1-enecarboxylic acid,
- 2-((2',3,4'-trimethoxy-[1,1'-biphenyl]-4-yl)carbamoyl)cyclopent-1-enecarboxylic acid,
- 2-((3'-ethoxy-3-methoxy-[1,1'-biphenyl]-4-yl)carbamoyl)cyclopent-1-enecarboxylic acid,
- 2-((3,3'-dimethoxy-[1,1'-biphenyl]-4-yl)carbamoyl)cyclopent-1-enecarboxylic acid,
- 2-((3,5-dibromo-4-((2-chloro-6-fluorobenzyl)oxy)phenyl)carbamoyl)cyclopent-1-enecarboxylic acid,
- 4-((2'-chloro-[1,1'-biphenyl]-4-yl)carbamoyl)-2,5-dihydrothiophene-3-carboxylic acid,
- 2-((4-(m-tolylthio)phenyl)carbamoyl)cyclopent-1-enecarboxylic acid,
- 2-((3'-(trifluoromethoxy)-[1,1'-biphenyl]-4-yl)carbamoyl)cyclopent-1-enecarboxylic acid,
- 2-((4-(benzo[b]thiophen-2-yl)phenyl)carbamoyl)cyclopent-1-enecarboxylic acid,
- 2-((4-(benzo[b]thiophen-2-yl)-2-fluorophenyl)carbamoyl)cyclopent-1-enecarboxylic acid,
- 2-((3'-ethoxy-3-fluoro-[1,1'-biphenyl]-4-yl)carbamoyl)cyclopent-1-enecarboxylic acid,
- 4-((3,5-difluoro-2'-methoxy-[1,1'-biphenyl]-4-yl)carbamoyl)-2,5-dihydrofuran-3-carboxylic acid,
- 2-((4-phenoxyphenyl)carbamoyl)cyclopent-1-enecarboxylic acid,
- 4-((3,5-dibromo-4-((2-chloro-6-fluorobenzyl)oxy)phenyl)carbamoyl)-2,5-dihydrothiophene-3-carboxylic acid,
- 2-((3-chloro-2'-methoxy-[1,1'-biphenyl]-4-yl)carbamoyl)cyclopent-1-enecarboxylic acid,
- 2-((2-chloro-2'-methoxy-[1,1'-biphenyl]-4-yl)carbamoyl)cyclopent-1-enecarboxylic acid,
- 2-((2,3,5,6-tetrafluoro-2'-methoxy-[1,1'-biphenyl]-4-yl)carbamoyl)cyclopent-1-enecarboxylic acid,
- 2-((2'-methoxy-3-methyl-[1,1'-biphenyl]-4-yl)carbamoyl)cyclopent-1-enecarboxylic acid,
- 2-((3,5-dichloro-2'-methoxy-[1,1'-biphenyl]-4-yl)carbamoyl)cyclopent-1-enecarboxylic acid,
- 2-((2'-ethoxy-3,5-difluoro-[1,1'-biphenyl]-4-yl)carbamoyl)cyclopent-1-enecarboxylic acid,
- 2-((3'-ethoxy-3,5-difluoro-[1,1'-biphenyl]-4-yl)carbamoyl)cyclopent-1-enecarboxylic acid,
- 2-((3,5-difluoro-3'-(trifluoromethoxy)-[1,1'-biphenyl]-4-yl)carbamoyl)cyclopent-1-enecarboxylic acid,
- 2-((2'-chloro-3,5-difluoro-[1,1'-biphenyl]-4-yl)carbamoyl)cyclopent-1-enecarboxylic acid,
- 2-((2',3,5-trifluoro-[1,1'-biphenyl]-4-yl)carbamoyl)cyclopent-1-enecarboxylic acid,
- 2-((3,5-difluoro-2',4'-dimethoxy-[1,1'-biphenyl]-4-yl)carbamoyl)cyclopent-1-enecarboxylic acid,
- 2-((3-chloro-4-((2-(trifluoromethyl)benzyl)oxy)phenyl)carbamoyl)cyclopent-1-enecarboxylic acid,
- 2-((3-chloro-4-((2-chloro-6-fluorobenzyl)oxy)phenyl)carbamoyl)cyclopent-1-enecarboxylic acid, 2-((4-(benzyloxy)-3-chlorophenyl)carbamoyl)cyclopent-1-enecarboxylic acid, 2-((3-chloro-4-((2-fluorobenzyl)oxy)phenyl)carbamoyl)cyclopent-1-enecarboxylic acid, or 2-(((3-fluoro-2'-methoxy-[1,1'-biphenyl]-4-yl)oxy)carbonyl)cyclopent-1-enecarboxylic acid.

15. A pharmaceutical composition according to claim 9, wherein said a salt or hydrate thereof is a calcium salt or hydrate of 2-(3-fluoro-3'-methoxy-biphenyl-4-ylcarbamoyl)-cyclopent-1-enecarboxylic acid.

16. A method for treating rheumatism, an acute immunological disorder, an autoimmune disease, a disease caused by malignant cell proliferation, an inflammatory disease, a disease caused by protozoal infestations in humans and animals, a disease caused by viral infection and *Pneumocystis carinii*, fibrosis, uveitis, rhinitis, asthma or athropathy, comprising administering to a subject in need thereof an effective amount of a salt or hydrate thereof according to claim 1.

17. The method according to claim 16, wherein said method is for the treatment of a graft versus host or host versus graft reaction, rheumatoid arthritis, multiple sclerosis, lupus erythematosus, inflammatory bowel disease, or psoriasis.

18. A method for the treatment of ankylosing spondylitis, autoimmune thyroiditis, coeliac disease, Grave's disease, Crohn's disease, ulcerative colitis, diabetes mellitus type 1, systemic lupus erythematosus, multiple sclerosis, vitiligo, osteoarthritis, psoriasis, psoriatic arthritis or rheumatoid arthritis, comprising administering to a patient in need thereof an effective amount of a compound according to claim 1.

19. A process for the preparation of a calcium salt or hydrate thereof as defined in claim 1, said process comprising:

a) adding a suspension of calcium hydroxide in an organic solvent to a solution of the free acid of a compound of formula (I), b) stirring the suspension obtained in a), c) at least partially evaporating said organic solvent to obtain a suspension of the calcium salt of said compound of formula (I), d) recovering the calcium salt of said compound of formula (I) from the mixture obtained in c), and e) washing the calcium salt of said compound of formula (I) obtained in d), with said organic solvent.

\* \* \* \* \*

UNITED STATES PATENT AND TRADEMARK OFFICE
CERTIFICATE OF CORRECTION

| | | |
|---|---|---|
| PATENT NO. | : 8,653,138 B2 | Page 1 of 1 |
| APPLICATION NO. | : 13/174899 | |
| DATED | : February 18, 2014 | |
| INVENTOR(S) | : Ammendola et al. | |

It is certified that error appears in the above-identified patent and that said Letters Patent is hereby corrected as shown below:

Title Page of Patent, (73) Assignee: reads "4SC MG, Planegg-Martinsried (DE)" should read -- 4SC AG, Planegg-Martinsried (DE) --.

In the Specification:

Column 33, Line 64 reads "Potassium salt   0.96   1.09" should read
-- Potassium salt   1.03   1.09 --.

Signed and Sealed this
Twenty-seventh Day of May, 2014

Michelle K. Lee
*Deputy Director of the United States Patent and Trademark Office*